(12) United States Patent
Matsumura et al.

(10) Patent No.: US 8,395,363 B2
(45) Date of Patent: Mar. 12, 2013

(54) HIGH VOLTAGE GENERATION CIRCUIT, PUNCTURE DEVICE, AND BLOOD TEST DEVICE

(75) Inventors: Keisuke Matsumura, Ehime (JP); Toshiki Matsumoto, Ehime (JP)

(73) Assignee: Panasonic Corporation, Osaka (JP)

( * ) Notice: Subject to any disclaimer, the term of this patent is extended or adjusted under 35 U.S.C. 154(b) by 405 days.

(21) Appl. No.: 12/681,720

(22) PCT Filed: Oct. 14, 2008

(86) PCT No.: PCT/JP2008/002907
§ 371 (c)(1),
(2), (4) Date: Apr. 5, 2010

(87) PCT Pub. No.: WO2009/047918
PCT Pub. Date: Apr. 16, 2009

(65) Prior Publication Data
US 2010/0219769 A1    Sep. 2, 2010

(30) Foreign Application Priority Data

Oct. 11, 2007  (JP) .................................. 2007-265175
Oct. 11, 2007  (JP) .................................. 2007-265176

(51) Int. Cl.
*G05F 1/24*   (2006.01)
*A61B 18/20*  (2006.01)
*H05B 37/02*  (2006.01)

(52) U.S. Cl. ........ 323/259; 323/282; 323/283; 323/284; 323/287; 315/209 R; 315/209 CD; 315/211; 315/291; 600/576; 600/583; 606/10; 606/107

(58) Field of Classification Search .............. 315/209 R, 315/209 CD, 211, 291; 323/182, 183, 259, 323/282, 283, 284, 287; 600/576, 583
See application file for complete search history.

(56) References Cited

U.S. PATENT DOCUMENTS

| 4,952,864 | A | * | 8/1990 | Pless et al. ................... 323/299 |
| 5,447,522 | A | * | 9/1995 | Chang et al. ...................... 607/7 |
| 5,643,252 | A |   | 7/1997 | Waner et al. |
| 5,749,904 | A |   | 5/1998 | Gliner et al. |

(Continued)

FOREIGN PATENT DOCUMENTS

| EP | 1997433 | 12/2008 |
| EP | 1997434 | 12/2008 |

(Continued)

*Primary Examiner* — Douglas W Owens
*Assistant Examiner* — Thai Pham
(74) *Attorney, Agent, or Firm* — Greenblum & Bernstein, P.L.C.

(57) ABSTRACT

A high voltage generation circuit for laser puncture in which the voltage for laser puncture can be boosted up to the laser oscillation level in a short time with low power loss. The high voltage generation circuit drives a laser unit for puncturing the skin by oscillating laser light. In the high voltage generation circuit, a capacitor is charged to supply power to the laser unit. A booster circuit supplies a current to the capacitor, and a voltage measurer measures the voltage of the capacitor. A controller controls the booster circuit based on an instruction from a user or the voltage of the capacitor to start precharge of the capacitor with a first current value at a first timing, and to start main charging of the capacitor with a second current value higher than the first current value at a second timing, later than the first timing.

26 Claims, 25 Drawing Sheets

U.S. PATENT DOCUMENTS

| | | | |
|---|---|---|---|
| 5,959,371 A * | 9/1999 | Dooley et al. | 307/130 |
| 6,650,091 B1 * | 11/2003 | Shiue et al. | 320/166 |
| 6,909,915 B2 * | 6/2005 | Greatbatch et al. | 607/5 |
| 6,990,903 B2 * | 1/2006 | Butland | 101/333 |
| 2009/0043227 A1 | 2/2009 | Fujiwara et al. | |
| 2009/0177117 A1 | 7/2009 | Amano et al. | |
| 2009/0281455 A1 | 11/2009 | Fujiwara et al. | |
| 2009/0318834 A1 | 12/2009 | Fujiwara et al. | |
| 2010/0106144 A1 * | 4/2010 | Matsumura et al. | 606/10 |

FOREIGN PATENT DOCUMENTS

| | | |
|---|---|---|
| EP | 1997435 | 12/2008 |
| JP | 2000-162677 | 6/2000 |
| JP | 2003-038662 | 2/2003 |
| JP | 2004-195245 | 7/2004 |
| JP | 2007-108192 | 4/2007 |
| WO | 2007/108515 | 9/2007 |
| WO | 2007/108516 | 9/2007 |
| WO | 2007/108517 | 9/2007 |
| WO | 2007/108518 | 9/2007 |

* cited by examiner

US 8,395,363 B2

HIGH VOLTAGE GENERATION CIRCUIT, PUNCTURE DEVICE, AND BLOOD TEST DEVICE

TECHNICAL FIELD

The present invention relates to a high-voltage generating circuit that drives a laser puncturing device, a puncturing apparatus using this high-voltage generating circuit and a blood test apparatus using this puncturing apparatus.

BACKGROUND ART

Diabetic patients need to measure their blood sugar level on a regular basis to maintain a normal blood sugar level by injecting insulin, dieting and so forth based on the measured blood sugar level. Therefore, patients need to always carry measuring instruments and measure their blood sugar level by themselves on a daily basis. For that purpose, patients puncture the skin of their fingers and so forth using a puncturing apparatus and measure their blood sugar level by making blood exuding from the skin contact a blood sugar measuring device. Biological information, such as lactic acid, hemoglobin A1C and so forth, is measured using blood obtained by the puncturing apparatus as well as the blood sugar level.

Although a puncturing apparatus with a needle has grown popular today, the risk of infection and so forth has been regarded as important and therefore a puncturing apparatus having a laser puncturing device using laser light has been known. This conventional high-voltage generating circuit 1 that drives the conventional laser puncturing apparatus is configured by: switch 3 connected to battery 2; boost circuit 4 connected to this switch 3; capacitor 6 connected to the output of this boost circuit 4 and connected to flash lamp (used as an exemplary light source) 5a constituting laser puncturing device 5; trigger switch 7a that is connected to the output of boost circuit 4 and is operated by the patient to generate a trigger signal; and trigger circuit 7 connected to this trigger switch 7a, as shown in FIG. 1. This trigger circuit 7 is connected to trigger electrode 5b provided in flash lamp 5a.

Here, a lithium-ion battery having an electromotive force of 3.7V is used as battery 2, and a capacitor of 300 μF is used as capacitor 6. Then, boost circuit 4 charges capacitor 5 with a charging current of 1.2 A, and laser puncturing device 5 has an oscillation voltage of 400 V and the minimum oscillation voltage of 300 V.

In this high-voltage generating circuit 1, an output current of battery 2 is inputted to capacitor 6 through boost circuit 4 and therefore capacitor 6 is charged. Along with charging to capacitor 6, the terminal voltage of capacitor 6 rises. By this means, the voltage applied across flash lamp 5a also rises.

The voltage applied across flash lamp 5a rises to the oscillation voltage (about 400 V) by charging for about seven seconds, and then, the patient turns on trigger switch 7a. Therefore, flash lamp 5a lights on, and this light energy 5d excites laser crystal 5e. Laser light 5f is emitted from laser crystal 5e, passes through lens 5g and then punctures skin 9. When skin 9 is punctured, blood 10 exudes from skin 9.

Here, Patent Document 1 and Patent Document 2 have been known as prior art document information relating to the invention of this application.
Patent Document 1: Japanese Patent Application Laid-Open No. 2003-38662
Patent Document 2: Japanese Patent Application Laid-Open No. 2004-195245

DISCLOSURE OF INVENTION

Problems to be Solved by the Invention

However, with the above-described high-voltage generating circuit 1, it takes seven seconds or more to make the voltage of capacitor 6 the oscillation voltage after capacitor 6 is charged. That is, to emit laser light of the preset intensity by turning on trigger switch 7a, the patient has to wait for seven seconds or more after turning on switch 3.

Now, this situation will be described in detail. FIG. 2 is a drawing showing the relationship between the current to charge capacitor 6 (charging current) and the duration required for this charging (charging duration) and the power loss at that time. As shown in FIG. 2, the charging current is inversely proportional to the charging duration and the power loss. That is, as shown in characteristic curve C1, when the charging current becomes larger (the right side in FIG. 2), the charging duration required for charging is shorter (the lower part in FIG. 2), and when the charging current becomes smaller, the charging duration required for charging is longer.

Meanwhile, when the charge current becomes larger due to the internal resistance of battery 2 indicated by characteristic curve C2, the power loss caused by the internal resistance increases (the upper part in FIG. 2), and when the charging current becomes smaller, the power loss is lower. Here, the power loss increases in proportion to the square of the charging current.

Therefore, although the charging duration becomes shorter by increasing the charging current of capacitor 6, the power loss increases and the load on the battery also increases, which cause the battery life to shorten. This is a serious problem in medical equipment. Puncturing can not be performed when necessary for the patient, which may cause the condition of the patient to significantly deteriorate.

Considering this balance between the power loss caused by the internal resistance of the battery and the charging duration required for charging, there is a demand to minimize the duration to charge a capacitor while minimizing the power loss of the battery and the amount of the charging current. For example, a current to charge the capacitor (charging current) is set to 1.2 A, and according to this setting, the duration required for charging (charging duration) is seven seconds. There is a demand to further shorten this duration. Here, despite being in an antithetical relationship, the power loss of the battery at this time is 7.06 J and there is also a demand to decrease of this power loss.

It is therefore an object of the present invention to provide a high-voltage generating circuit for laser puncturing that allows the voltage for laser puncturing to rise to a laser oscillation level with a low power loss and in a short period of time, a puncturing apparatus and a blood test apparatus.

The high-voltage generating circuit according to the present invention is a high-voltage generating circuit that drives a laser puncturing unit that oscillates laser light and punctures skin. The high-voltage generating circuit has a configuration including: a capacitor that is charged with an electric charge and supplies power to the laser puncturing unit; a boost circuit that supplies a current to the capacitor; a voltage measuring section that measures a voltage of the capacitor; a control section that controls the boost circuit based on a command from a user or the voltage of the capacitor. The control section starts charging the capacitor with a current of a first value at a first timing, and starts charging the capacitor with the current of a second value higher than the first value at a second timing later than the first timing.

The high-voltage generating circuit according to the present invention is a high-voltage generating circuit that drives a laser puncturing unit that oscillates laser light and punctures skin. The high-voltage generating circuit has a configuration including: a plurality of capacitors that are charged with electric charges and supply power to the laser puncturing unit; a switching section that switches a connection state of the plurality of capacitors between serial connection and parallel connection; a boost circuit that supplies a current to the plurality of capacitors; a voltage measuring circuit that measures a voltage of the plurality of capacitors; a control section that controls the boost circuit and the switching section based on a command from a user or the voltage of the capacitors. The control section makes the boost circuit start charging the plurality of capacitors in a state in which the plurality of capacitors are connected in parallel by switching the switching section at a first timing, and connects the plurality of capacitors in series by switching the switching section at a second timing later than the first timing.

The puncturing apparatus has a configuration including a high-voltage generating circuit and a laser puncturing unit having the above-described configuration.

The blood test apparatus according to the present invention has a configuration including a puncturing apparatus having the above-described configuration and a blood sensor that analyzes a blood component exuding from punctured skin.

Advantageous Effects of Invention

According to the present invention, the voltage for laser puncturing can be raised to a laser oscillation level with a low power loss and in a short period of time.

BEST MODE FOR CARRYING OUT THE INVENTION

Now, embodiments of the present invention will be described in detail with reference to the accompanying drawings.

(Embodiment 1)

Figure 1:
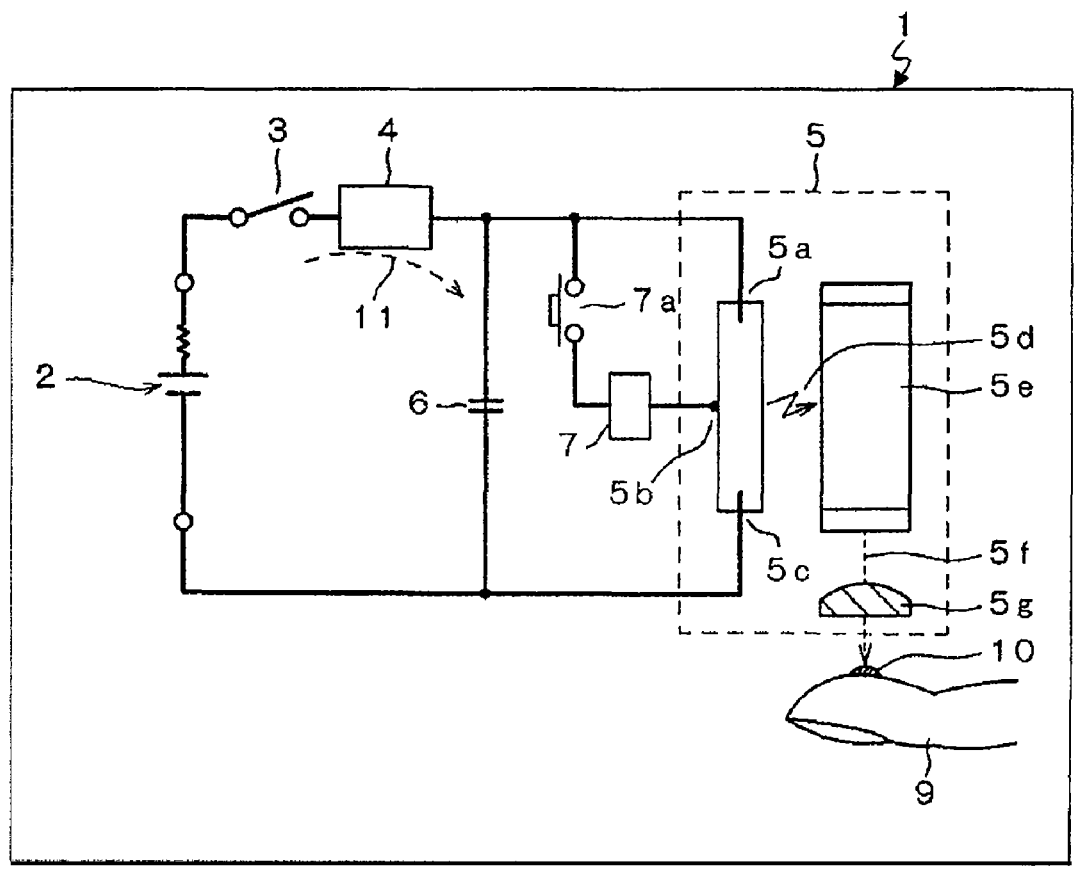
FIG. 1 is a block diagram showing a conventional high-voltage generating circuit and its neighborhood.
Figure 2:
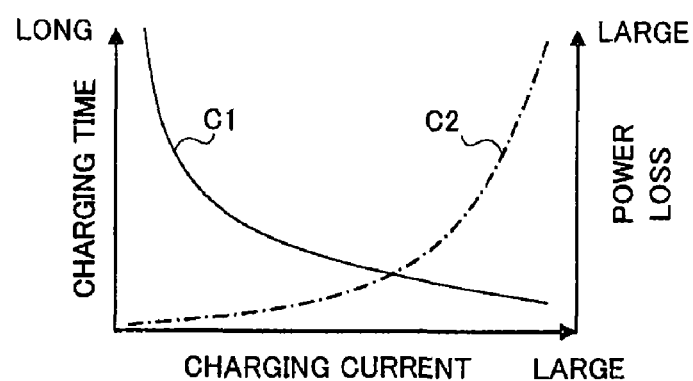
FIG. 2 is a characteristic chart of the conventional high-voltage generating circuit and its neighborhood.
Figure 3:
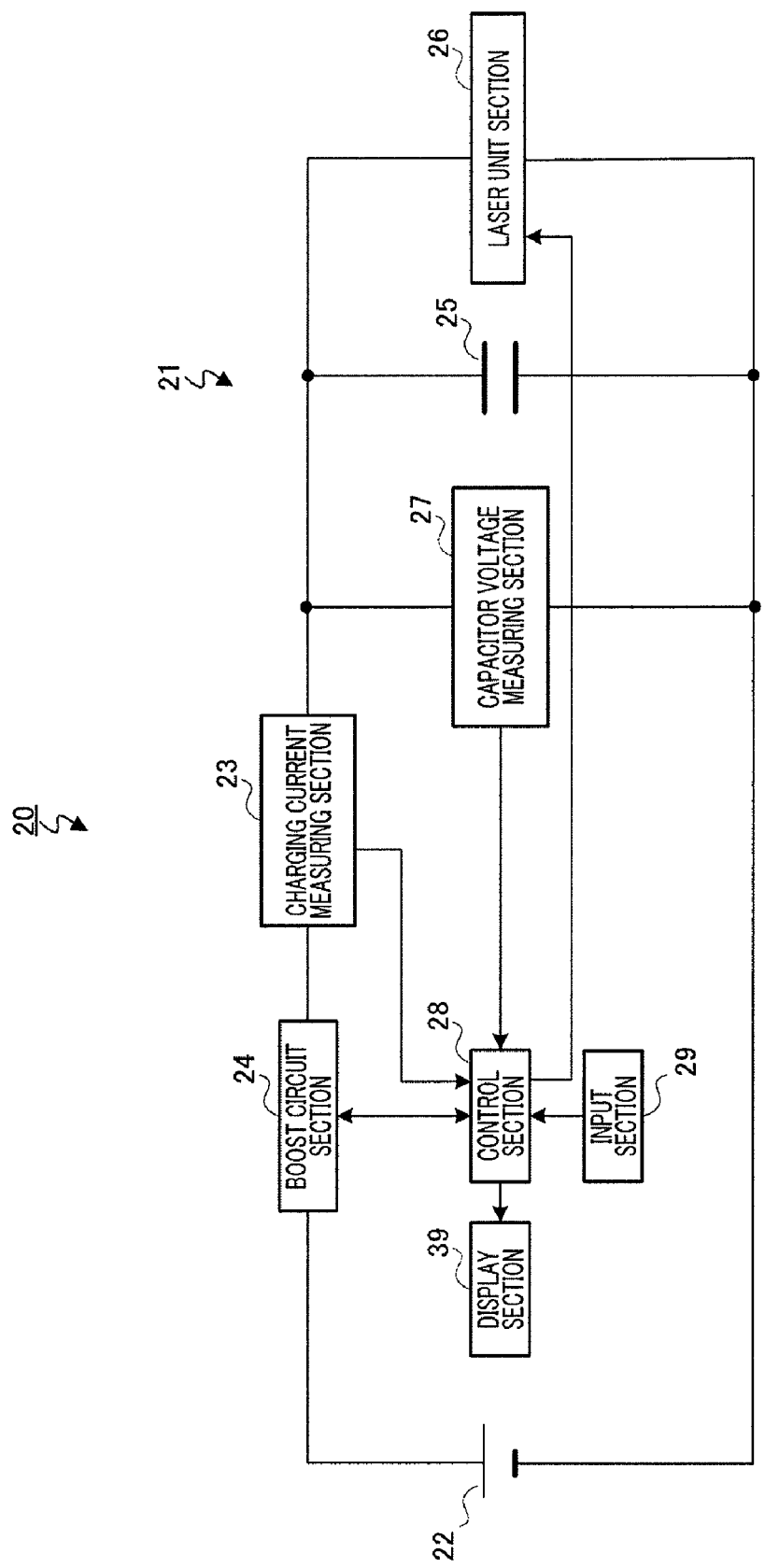
FIG. 3 is a block diagram showing a configuration of primary parts of a puncturing apparatus having a high-voltage generating circuit according to embodiment 1 of the present invention.

FIG. 3 is a block diagram showing a configuration of primary parts of puncturing apparatus 20 having high-voltage generating circuit 21 according to embodiment 1. Puncturing apparatus 20 has high-voltage generating circuit 21, battery 22 and laser unit section (laser puncturing unit) 26.

The input of high-voltage generating circuit 21 is connected to battery 22 and the output of high voltage generating circuit 21 is connected to laser unit section 26.

Here, although a secondary battery having an internal resistance of $0.7\Omega$ and an electromotive force of 3.7 V is used as battery 22, battery 22 is not limited to a secondary battery and a primary battery may be used as battery 22. With the present embodiment, a lithium-ion battery is used as a secondary battery. Except for this, a nickel metal hydride battery, a nickel cadmium battery and so forth are used as a secondary battery. Here, a lithium battery, a manganese dry battery, an alkaline dry battery and so forth are used as a primary battery, and any of them can be used. Battery 22 is connected to the input of boost circuit section 24 in high-voltage generating circuit 21 and supplies power to capacitor 25 in high-voltage generating circuit 21 through boost circuit section 24.

High-voltage generating circuit 21 has boost circuit section 24, charging current measuring section 23, capacitor 25, capacitor voltage measuring section 27, control section 28, input section 29 and display section 39.

Charging current measuring section 23 measures the current outputted from boost circuit section 24 and outputs the measurement result to control section 28.

Boost circuit section 24 outputs a voltage higher than the input voltage. The input side of boost circuit section 24 is connected to the positive side of battery 22. The output side of boost circuit section 24 is connected to one end of capacitor 25 through charging current measurement section 23. That is, capacitor 25 is connected between the output of boost circuit section 24 and the negative side of battery 22 through charging current measuring section 23. Here, boost circuit section 24 is connected to charging current measuring section 23 in its output side.

Here, boost circuit section 24 can change the inputted voltage of 3 to 5V to 200 to 700 V to raise the voltage.

Figure 4:
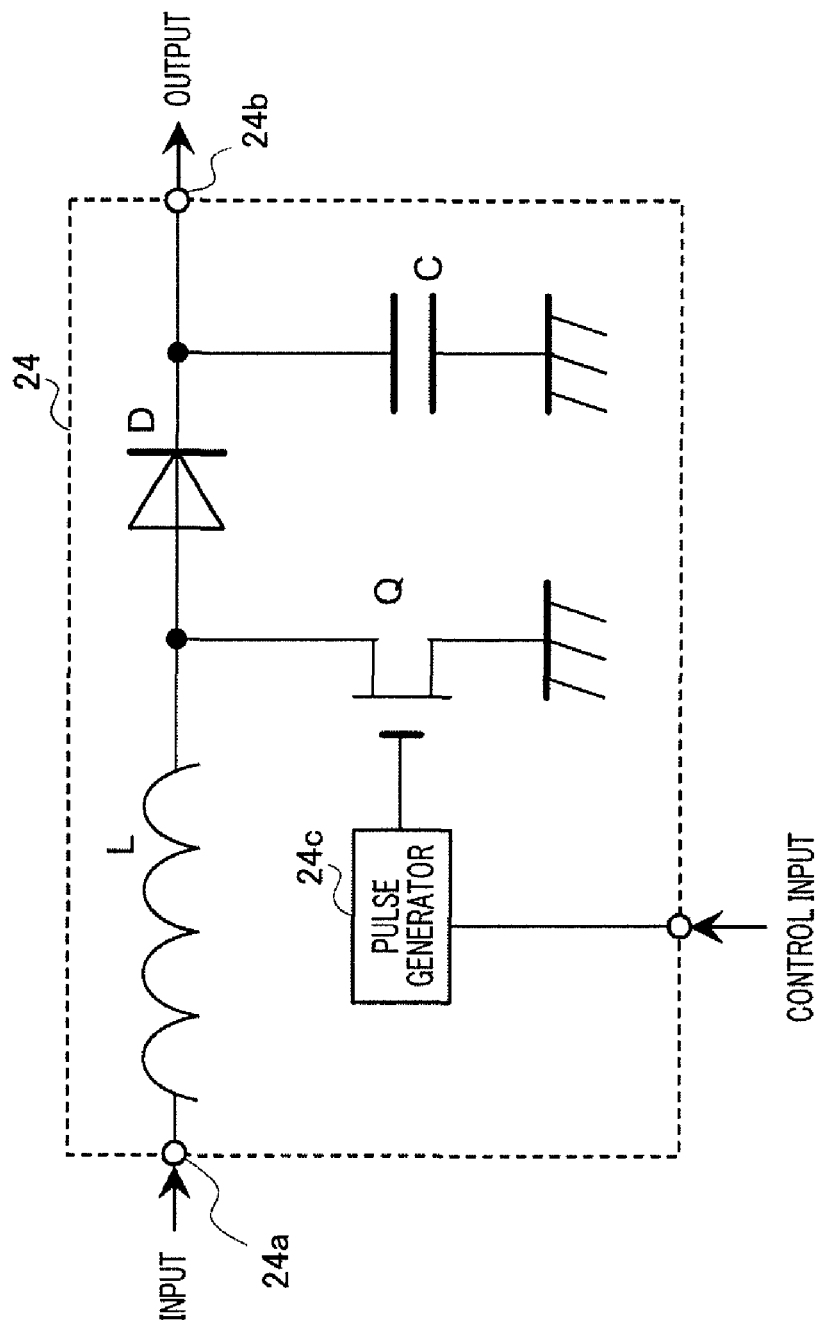
FIG. 4 is a block diagram showing an exemplary configuration of a boost circuit section.
Figure 5:
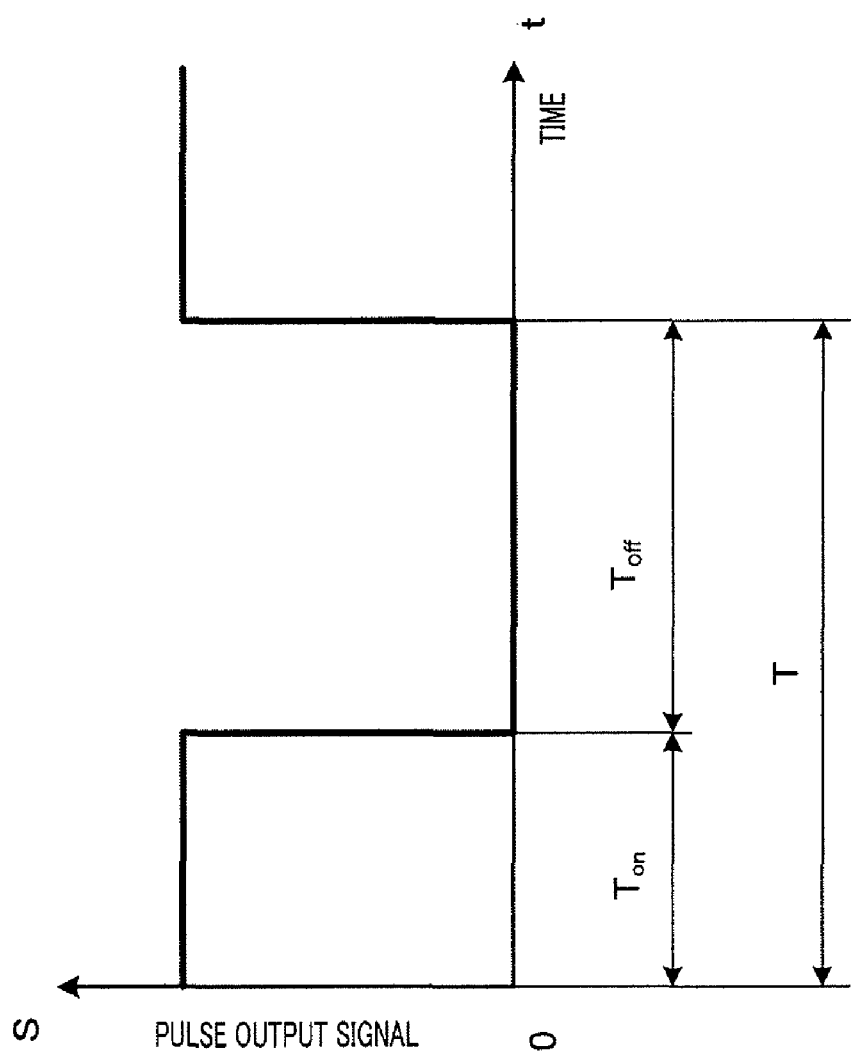
FIG. 5 is a drawing a pulse waveform outputted from a pulse generator shown in FIG. 4.

FIG. 4 is a block diagram showing an exemplary configuration of boost circuit section 24 and FIG. 5 is a drawing showing a pulse waveform outputted from a pulse generator shown in FIG. 4.

The convertor shown in FIG. 4 as boost circuit section 24 raises the inputted voltage and outputs the raised voltage, and here, a boost chopper circuit is used as boost circuit section 24. In boost circuit section 24, a switching output end of switching transistor Q and one end of rectifying diode D are connected to current smoothing inductance L to which a voltage from battery 22 is inputted through input section 24a. Voltage smoothing capacitor C and output terminal section 24b are connected to the other end of rectifying diode D. In addition, pulse generator 24c is connected to the switching input end of switching transistor Q. External control section 28 (see FIG. 3) is connected to this pulse generator 24c. Pulse generator 24c outputs pulses to switching transistor Q by receiving a control input signal from control section 28 as input.

When the control input signal is received as input, pulse generator 24c generates the pulse wave to change the proportion of on-time Ton for a predetermined period (1 kHz to 40 kHz) as shown in FIG. 5. The output voltage or current is changed through switching transistor Q based on this proportion of the on-time.

Charging current measuring section 23 connected to the output side of this boost circuit section 24 measures the current outputted from boost circuit section 24 and inputted to capacitor 25. Here, the output end of charging current measuring section 23 is connected to battery 22 (the negative side of battery 22) through capacitor 25, laser unit section 26 and capacitor voltage measuring section 27.

Capacitor 25 is charged with electricity (electric charge) outputted from boost circuit section 24 and therefore becomes the power supply for laser unit section 26. A capacitor input power supply section of laser unit section 26 and capacitor voltage measuring section 27 are connected to both ends of capacitor 25. For example, a capacitor having an electrostatic capacity of 300 µF and a withstand voltage of 500 V may be used as capacitor 25.

Figure 6:
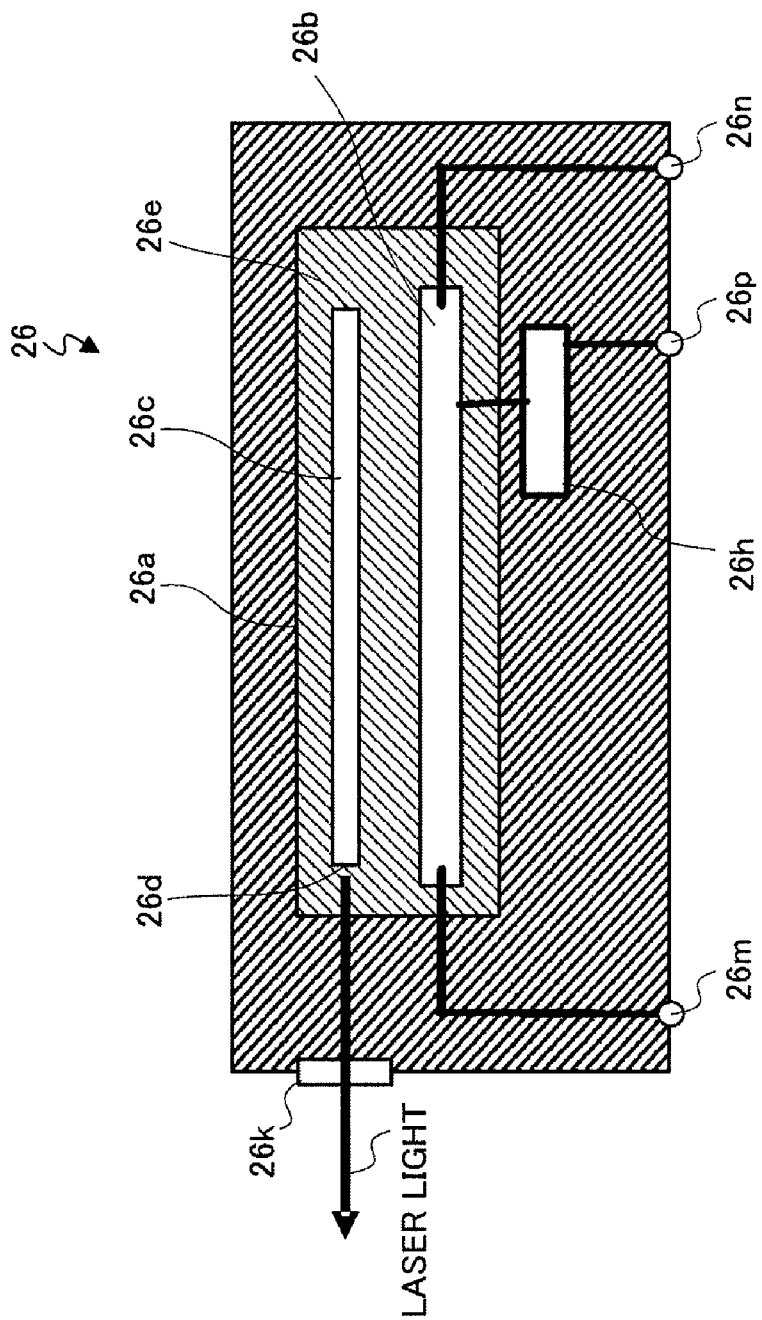
FIG. 6 is a block diagram of a laser unit section.

FIG. 6 is a block diagram of laser unit section 26.

In laser unit section 26 shown in FIG. 6, lens-barrel 26a has a circular or elliptical tubular shape, and its inner circumference surface is finished as a mirror surface in order to reflect the light source efficiently.

Here, lens-barrel 26a is formed to make an elliptical shape to provide a confocal system, flash lamp 26b (an example of light source) is placed on one focal point of this lens-barrel 26a and laser rod 26c is placed on the other focal point. By this means, light is emitted from flash lamp 26b, and laser rod 26c is illuminated with this light efficiently.

First reflecting film 26d having a reflectivity of 85 to 95% is formed on one end surface of laser rod 26c. In addition, second reflecting film 26e having a reflectivity equal to or more than 99% is formed on the other end surface of laser rod 26c.

Flash lamp 26b is configured by enclosing therein xenon gas. Both ends of capacitor 25 are connected to both ends of this flash lamp 26b through first capacitor connecting section 26m and second capacitor connecting section 26n. In addition, trigger circuit section 26h is connected to flash lamp 26b.

Trigger circuit section 26h is connected to control section 28 through trigger signal input section 26p. Trigger circuit section 26h applies a voltage instantaneously to flash lamp 26b to which a high-voltage is applied from capacitor 25 by a trigger signal inputted from control section 28 through trigger signal input section 26p to make flash lamp 26b emit light.

That is, when capacitor 25 is charged such that the voltage of capacitor 25 is 200 V to 700 V, flash lamp 26b does not emit light because the inside of flash lamp 26 is insulated. When trigger circuit section 26h applies a voltage of 5 to 10 kV to flash lamp 26b instantaneously after this state, that is, after capacitor 25 applies the voltage of 200 to 700 kV across flash lamp 26b, inductive discharge starts in flash lamp 26b and then a current flows in flash lamp 26b from capacitor 25 and light is emitted from flash lamp 26b. This emitted light condenses into laser rod 26c by lens-barrel 26a.

As described above, the light focused by laser rod 26c excites doped laser activating material (Er:YAG in the present embodiment) existing in laser rod 26c to generate light having a wavelength of about 2.94 µm.

The generated light resonates in first reflecting film 26d and second reflecting film 26e and is amplified in laser rod 26c.

The amplified light having a higher intensity than a certain threshold passes through first reflecting film 26d and is outputted outside as laser output light (laser light) through exit hole 26k. Since laser rod 26c in which Er:YAG is doped is employed in laser unit section 26 according to the present embodiment, laser unit section 26 emits laser light having a laser wavelength of about 2.94 µm.

Here, a convex lens (not shown) is provided in front of exit hole 26k to allow laser light passing through to focus on the skin of the patient. When skin is punctured, blood exudes from the skin.

Returning to FIG. 3, capacitor voltage measuring section 27 is connected to battery 22 and both ends (input end and output end) of capacitor 25 to measure the voltage of capacitor 25. Here, capacitor voltage measuring section 27 is configured by an A/D (analog/digital) converter. Capacitor voltage measuring section 27 outputs the measured voltage value of capacitor 25 to control section 28.

Input section 29 is configured by a switch and so forth, and is connected to control section 28. When received from the patient as input, input section 29 notifies control section 28 of that, and control section 28 controls each section based on this notification.

Display section 39 is configured by LCD, LED and so forth, is connected to control section 28 and displays information inputted from control section 28 to make the patient confirm the information by sight.

Control section 28 determines the amount of charge (current value) to capacitor 25 based on the input from charging current measuring section 23 and capacitor voltage measuring section 27, and outputs a command signal to output the determined amount of charge to boost circuit section 24. Control section 28 controls the amount of current and the boosted voltage outputted from boost circuit section 24 by outputting the control signal to this boost circuit section 24. In addition, control section 28 outputs a trigger signal to control the emission of laser light to trigger signal input section 26p based on the input from each section to make laser unit section 26 emit laser light.

As described above, control section 28 controls the charge state of capacitor 25 and also controls the timing laser light is emitted.

Control section 28 controls the charge state of capacitor 25 to control the voltage to be the puncturing laser oscillation voltage (second charging voltage) for oscillating laser light, which allows laser unit section 26 to perform puncturing.

To be more specific, control section 28 controls boost circuit section 24 at a predetermined timing, starts charging capacitor 25 with the current of a first current value, and charges capacitor 25 with the current of a second current value larger than the first current value after capacitor 25 is charged with the current of the first current value.

Here, the first current value is a current value at the time until the voltage (first threshold) equal to or more than the voltage (minimum laser oscillation voltage) allowing laser unit section 26 to perform laser oscillation is applied to capacitor 25 as the power supply section to laser unit section 26. That is, the first current value is the value for applying, to capacitor 25 through boost circuit section 24, a voltage not to emit laser light from laser unit section 26. Controlling boost circuit section 24 using this first current value by control section 28 is referred to as "preliminary charging" and a voltage equal to or lower than the voltage to perform laser oscillation in laser unit section 26 (voltage not to emit laser light) is referred to as "preliminary charging voltage (first charging voltage)". Control section controls boost circuit section 24 at the time the voltage reaches a voltage a little lower (e.g., 10 V lower) than the voltage to perform laser oscillation (minimum laser oscillation voltage) to stop supplying the current to capacitor 25.

This first current value is determined based on a unique configuration of laser unit section 26 (see FIG. 6). To be more specific, the first current value is determined based on the lamp diameter and the arc length of flash lamp 26b, the arrangement and the reflectivity of lens-barrel 26a, the resonator reflectivity, the diameter and the length of laser rod 26c, and so forth.

Here, the predetermined timing (start timing) at which control section 28 performs preliminary charging is as follows, for example: (1) "starting immediately after puncturing"; (2) "automatically starting by a learning function"; and (3) "starting by the patient to prepare for puncturing". Here, these three start timings will be described later.

In addition, the second current value is a current value to apply the puncturing laser oscillation voltage (second threshold) allowing laser unit section 26 to perform laser oscillation for puncturing, to capacitor 25, which is the power supply section for laser unit section 26. That is, the second current value is a value to apply, to capacitor 25 through boost circuit section 24, the voltage allowing laser unit section 26 to perform laser puncturing. Controlling boost circuit section 24 using this second voltage value by control section 28 is referred to as "main charging", and the puncturing laser oscillation voltage, which is a voltage allowing laser unit section 26 to perform laser puncturing, is referred to as "main charging voltage (second charging voltage)."

In addition, control section 28 outputs a trigger signal to laser unit section 26 in a state in which main charging has been completed and therefore preparation for emitting laser light that can puncture skin has been completed, and makes laser unit section 26 perform puncturing with laser oscillation. To be more specific, when information indicating that capacitor 25 is charged and the voltage of capacitor 25 reaches the puncturing laser oscillation voltage (puncturing laser oscillation voltage value) is received from capacitor voltage measuring section 27 as input, control section 28 outputs a trigger signal to trigger signal input section 26p. The trigger signal is inputted to trigger circuit section 26h through trigger signal input section 26p, so that laser light is emitted from laser unit section 26.

Moreover, control section 28 outputs, to display section 39, the input from each section, such as charging current measuring section 23 and capacitor voltage measuring section 27, and information indicating the determined amount of charge and so forth and reports the state of the system to the patient.

When voltage generating circuit 21 configured as described above activates, capacitor 25 is charged through boost circuit section 24. The current value of the charging at this time is a current for which the influence of the loss of battery 22 is lower. Capacitor 25 is charged until the voltage (e.g., 290 V) is equal to or lower than the laser oscillation voltage (e.g., about 300 V). That is, capacitor 25 is charged until the voltage becomes the preliminary charging voltage. Here, the voltage across capacitor 25 is measured by capacitor voltage measuring section 27. Laser unit section 26 does not emit laser light at this preliminary charging voltage and therefore safety is assured.

Next, for example, when the patient turns on the switch of input section 29, capacitor 25 is further charged from battery 22 through boost circuit section 24. At this time, capacitor 25 is charged until the voltage becomes the puncturing laser oscillation voltage (e.g., 400V). This allows laser unit section 26 to emit laser light having a predetermined intensity and therefore laser is emitted.

Figure 7:
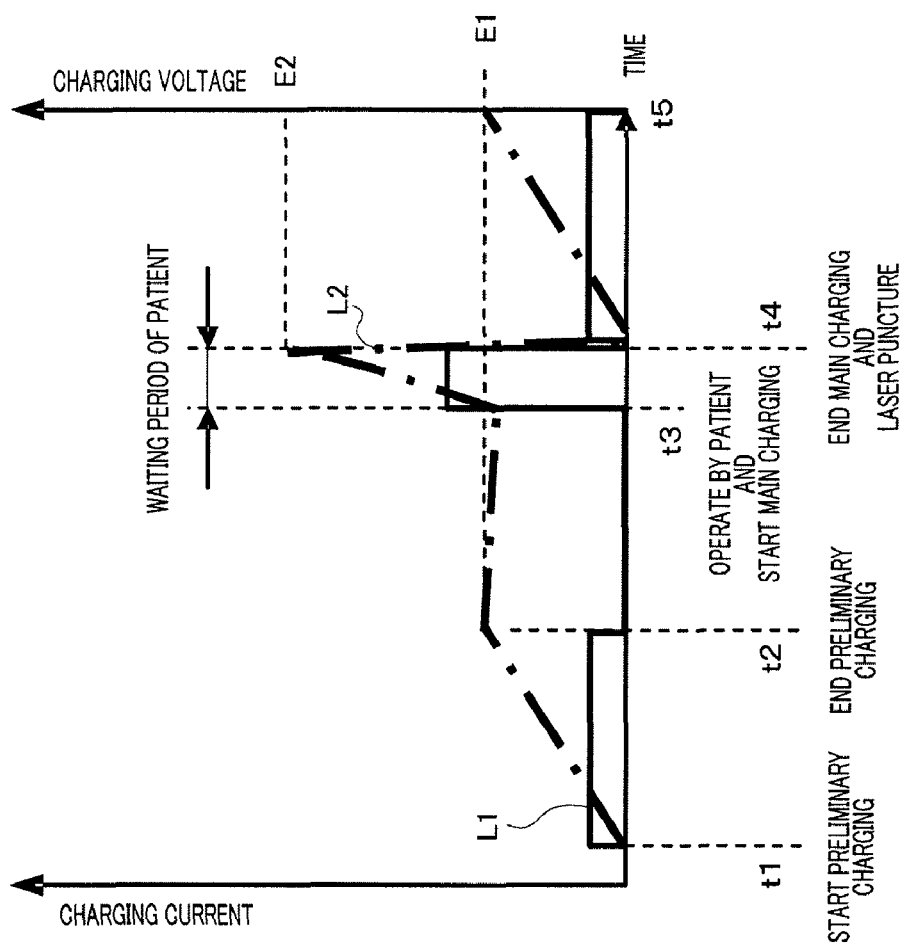
FIG. 7 is an operation timing chart explaining operations of the high-voltage generating circuit according to embodiment 1 of the present invention.

A case in which "puncturing is performed immediately after main charging" in the puncturing apparatus having this high-voltage generating circuit 21 will be described in terms of the time. FIG. 7 is an operation timing chart explaining operations of high-voltage generating circuit 21 according to embodiment 1 of the present invention. In FIG. 7, the horizontal axis shows time, the vertical axis shows the magnitude of the charging voltage and the charging current, solid line L1 shows the charging current and dashed line L2 shows the charging voltage.

When the system of high-voltage generating circuit 21 is activated, control section 28 starts the preliminary charging in capacitor 25 through boost circuit section 24 at time T1 for "start of preliminary charging." The charging current at this time is 100 mA to reduce the power loss of battery 22. In this state, control section 28 monitors the voltage across capacitor 25 through capacitor voltage measuring section 27.

It takes thirty-five seconds to charge capacitor 25 up to point t2 by controlling charging current L1 to be 0.1 A. That is, capacitor 25 is charged until the amount of charge to capacitor 25 is 290 V (preliminary charging voltage E1). The purpose for charging with a smaller current (0.1 A) than before is to make the power loss of battery 22 low. In addition, the purpose for controlling the amount of charge (L2) to 290 V below the minimum oscillation voltage (300 V) is not to emit laser light erroneously.

At time t2 "stopping the preliminary charging", which is the time the voltage of capacitor 25 becomes the preliminary charging voltage E1 (290 V in the present embodiment) equal to or lower than the laser oscillation level, control section 28 stops the preliminary charging to capacitor 25 through boost circuit section 24.

In this state, the system waits for operation by the patient, that is, input from input section 29, indicating "start of puncturing" (a command to perform puncturing including main charging) by pressing a switch such as a puncturing button.

When the puncturing button and so forth is pressed, a signal indicating the start of puncturing is inputted from input section 29 to control section 28. By this means, control section 28 starts main charging using boost circuit section 24 at time t3 for "operating the puncturing apparatus by the user" and "starting main charging." In main charging, the capacitor is charged with a current of 2 A in order to shorten the charging duration. In this state, control section 28 monitors the voltage across the capacitor using capacitor voltage measuring section 27 in the same manner as in preliminary charging. When the voltage of capacitor 25 becomes the main charging voltage E2 (e.g., 400 V), which is the puncturing laser oscillation voltage in the present embodiment, the system (control section 28) outputs a trigger signal to laser unit section 26 to make laser unit section 26 emit laser light. In FIG. 7, the point at which the voltage of capacitor 25 reaches the main charging voltage E2 is shown as time t4 indicating "finish of the main charging" and "laser puncturing."

Although the charging current for main charging is higher than before, the charging duration is shorter (2.7 seconds) above that, and therefore the power loss of battery 22 is low.

In addition, preferably, the patient can recognize the waiting period (e.g., two seconds) for this charging duration by a sounding section (not shown) such as a buzzer and display section 39. For example, when the voltage of capacitor 25 is measured to be the setting voltage through capacitor voltage measuring section 27, control section 28 make the sound section and display section 39 connected thereto sound the buzzer until point t4 and display that the main charging is in progress.

When laser light is emitted from laser unit section 26, the amount of charge in capacitor 25 is approximately zero and the system (control section 28) restarts preliminary charging using boost circuit section 24 in preparation for the next puncturing.

As described above, control section 28 measures the voltage across capacitor 25 through capacitor voltage measuring circuit section 27, and based on the measured voltage, identifies the preliminary charging voltage E1 and the laser oscillation voltage E2 and controls boost circuit section 24. Consequently, the voltage of capacitor 25 for laser puncturing can be raised to the laser oscillation level with the lower power loss and in a short time.

For example, since preliminary charging is performed with the present embodiment, the waiting period after the trigger switch (a part of input section 29) is turned on until laser light is emitted, is short, 2.7 seconds. In addition, since the time required for preliminary charging is short although the main charging current is large, the overall power loss of battery 22 becomes low. Generally, the charging energy Qc of capacitor 25 is indicated by equation 1.

$$Q_c = \frac{1}{2}CV_c^2 \quad \text{(Equation 1)}$$

where, Vc: capacitor voltage

Energy required to charge capacitor 25 to the oscillation voltage of 400 V is 24 J assuming that the electrostatic capacity of capacitor 25 is 300 μF and the voltage Vc is 400 V. Here, the loss in boost circuit section 24 is low and therefore is ignored. In addition energy Qb charged to capacitor 25 is indicated by equation 2.

$$Q_b = V_b I t - r I^2 t \quad \text{(Equation 2)}$$

where, $V_b$ I t: energy flowing from the battery
r $I^2$ t=loss energy

In this equation 2, Vb·I·t is the energy flowing out from battery 22 and r·I square·t is the energy consumed by battery 22. In equation 2, the charging duration for conventional high-voltage generating circuit 1 is seven seconds when the current is 1.2 A, so that the loss is about 7.06 J.

On the other hand, in preliminary charging according to the present embodiment, the preliminary charging duration is thirty-five seconds when a preliminary charging voltage E1 is 290 V and a current is 0.1 A, so that the loss is 0.25 J. In addition, when a main charging voltage (laser oscillation voltage E2) for main charging is 400 V and a current is 1.7 A, the main charging duration is 2.7 seconds, so that the loss is 5.46 J. This comparison is shown in table 1.

TABLE 1

|  | Past | Present embodiment | | |
|---|---|---|---|---|
|  |  | Preliminary charging | Main charging | Total |
| Charging time [s] | 7 | 35 | 2.7 | 37.2 |
| Loss [J] | 7.06 | 0.25 | 5.46 | 7.71 |

As described above, in the present embodiment, the total loss is 5.71 J and the waiting period from which the user starts charging operation is 2.7 seconds. Thus, the waiting period and loss are improved than those of conventional high-voltage generating circuit 1.

With the present embodiment, the user can start puncturing immediately after (2.7 seconds) charging start operation by starting preliminary charging at the time the previous puncturing is completed.

That is, in the puncturing apparatus having high-voltage generating circuit 21, preliminary charging is started immediately after puncturing to prepare for the next puncturing, and therefore, the puncturing apparatus is suitable for the patient who frequently use the apparatus in a day and for a case in which the apparatus is continuously used in a hospital and so forth.

In order to prevent power loss caused by discharge, this preliminary charging by control section 28 of high-voltage generating circuit 21 may not be started immediately after laser puncturing (equivalent to "starting immediately after puncturing"), but starting of preliminary charging may be determined by a learning function (equivalent to "automatically starting by a learning function"), or preliminary charging may be started by the patient to prepare for puncturing (equivalent to "starting by the patient to prepare for puncturing").

For example, when six hours pass (assuming that puncturing is performed after each meal) after preliminary charging, the charging voltage is reduced by about 30 V due to natural discharge. Energy is required in order to compensate for the loss cased by this natural discharge. In order to reduce this loss, for example, a learning function may be provided. That is, the time at which the patient performs puncturing is stored as time data using a timer and so forth, and preliminary charging is automatically started a little before the next expected puncturing time (calculated by past statistics) based on the time data. As a result of this, the loss can be reduced by an effect of preliminary charging.

As described above, high-voltage generating circuit 21 having a function for "automatically starting by a learning function" to record the everyday puncturing time of the patient and start preliminary charging at a predetermined time before the puncturing time.

Figure 8:
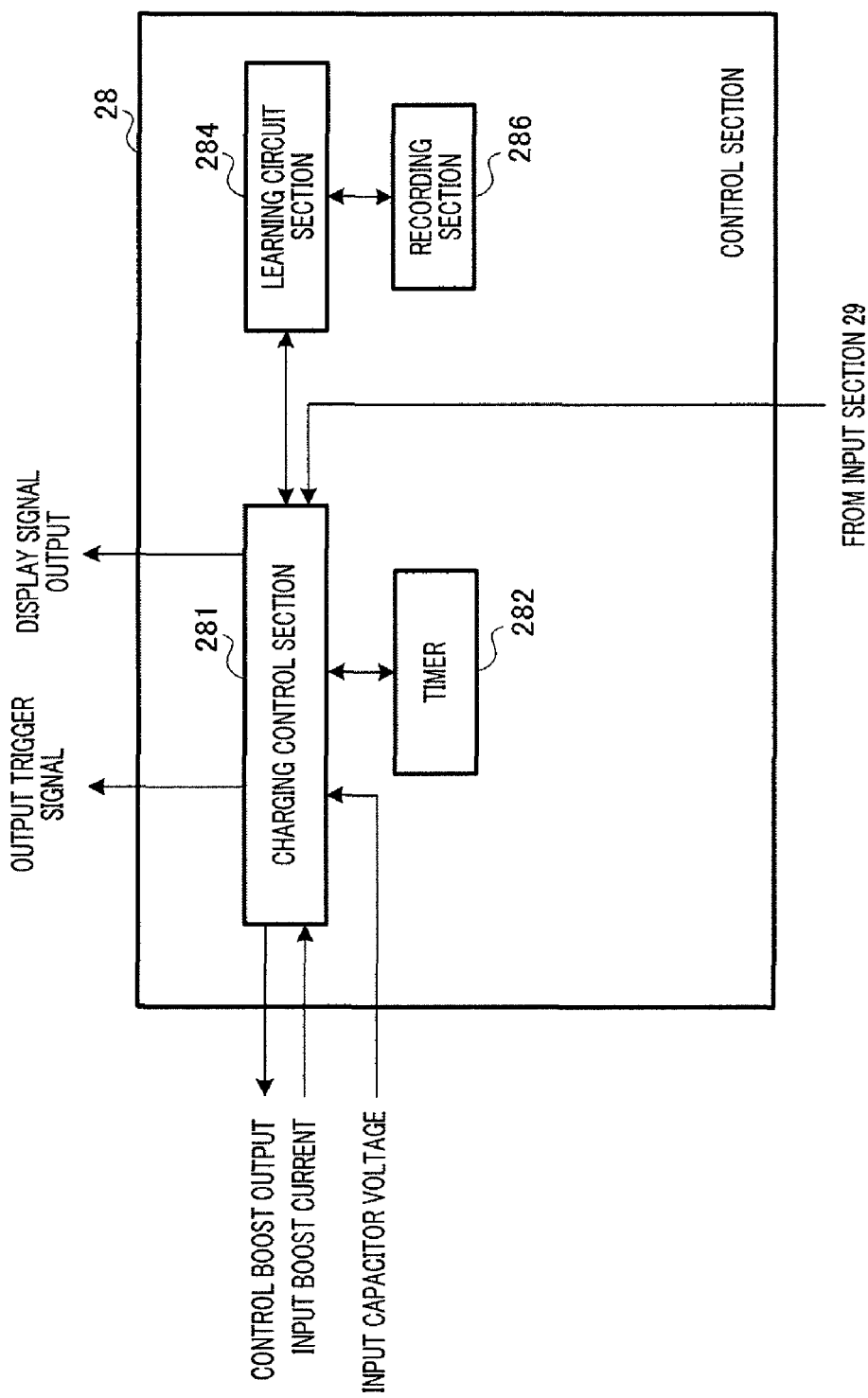
FIG. 8 is a functional block diagram showing a configuration of a control section.

FIG. 8 is a functional block diagram showing a configuration of control section 28.

Control section 28 has charging control section 281, timer 282, learning circuit section (puncturing timing learning section) 284 and recording section 286.

Charging control section 281 has a function of control section 28 described above, determines the amount of charge (current value) to capacitor 25 based on the input from charging current measuring section 23 and capacitor voltage measuring section 27 and outputs a command signal to output the determined amount of charge to boost circuit section 24. Charging control section 281 controls the amount of current and the boosted voltage outputted from charging control section 281.

That is, charging control section 281 controls boost circuit section 24 according to a command from the user through input section 29, or based on the voltage of the capacitor from capacitor voltage measuring section 27, and starts charging to capacitor 25 with the first current value at a preliminary charging starting timing inputted from outside (e.g., from input section 29 or learning circuit section 284).

In addition, charging control section 281 controls boost circuit section 24 to stop supplying the current to capacitor 25 at the time the voltage of capacitor 25 reaches, for example, the voltage 10 V lower than the voltage for performing laser oscillation (the minimum laser oscillation voltage).

Charging control section 281 controls boost circuit section 24 to start charging to capacitor 25 with the second current value higher than the first current value, at the main charging starting timing after the preliminary charging starting timing.

Thus, charging control section 281 issues a command to boost circuit section 24 based on the input from charging current measuring section 23 and capacitor voltage measuring section 27 to control the voltage or current of boost circuit section 24 to be an arbitrarily voltage or current.

In addition, charging control section 281 outputs, to trigger signal input section 26p, a trigger output signal to control emission of laser light by applying the laser oscillation voltage to capacitor 25 to make laser unit section 26 emit laser light.

Timer 282 measures the time of the system of high-voltage generating circuit 21 and outputs the measured time to charging control section 281, and therefore, the time to start preliminary charging is determined in charging control section 281 based on the outputted signal.

In addition, when charging control section 281 outputs, to laser unit section 26, a trigger signal for emitting laser light, the time at which the trigger signal is outputted is inputted to learning circuit section 284.

Charging control section 281 inputs a trigger signal output time, which is the time at which laser puncturing is performed to learning circuit section 284 and learning circuit section 284 outputs the inputted information to recording section 286 and stores it therein. Learning circuit section 284 estimates the time at which the patient uses the apparatus, using the data (data of the time at which laser puncturing is performed in the past) stored in recording section 286 and outputs a signal indicating the predetermined time before the estimated time at which the patient uses the apparatus to charging control section 281. Charging control section 281 outputs the boosted output control signal (the first current value) to boost circuit section 24 to control boost circuit section 24, and starts preliminary charging to capacitor 25.

The number of times the patient uses the apparatus (the number of times the blood sugar level is measured) varies, between one time and six times. However, since each time the puncturing apparatus is used is basically before and after meal, puncturing is performed substantially on a regular basis. The system of high-voltage generating circuit 21 to start preliminary charging by a learning function records each time at which puncturing is performed regularly and the preliminary charging is automatically started at the everyday predetermined time before the puncturing time (for example, before two hours.) A purpose for performing preliminary charging at an estimated time, that is, a predetermined time before the time the patient uses the puncturing apparatus is to absorb variation of the time at which the patient uses the puncturing apparatus every day.

Figure 9:
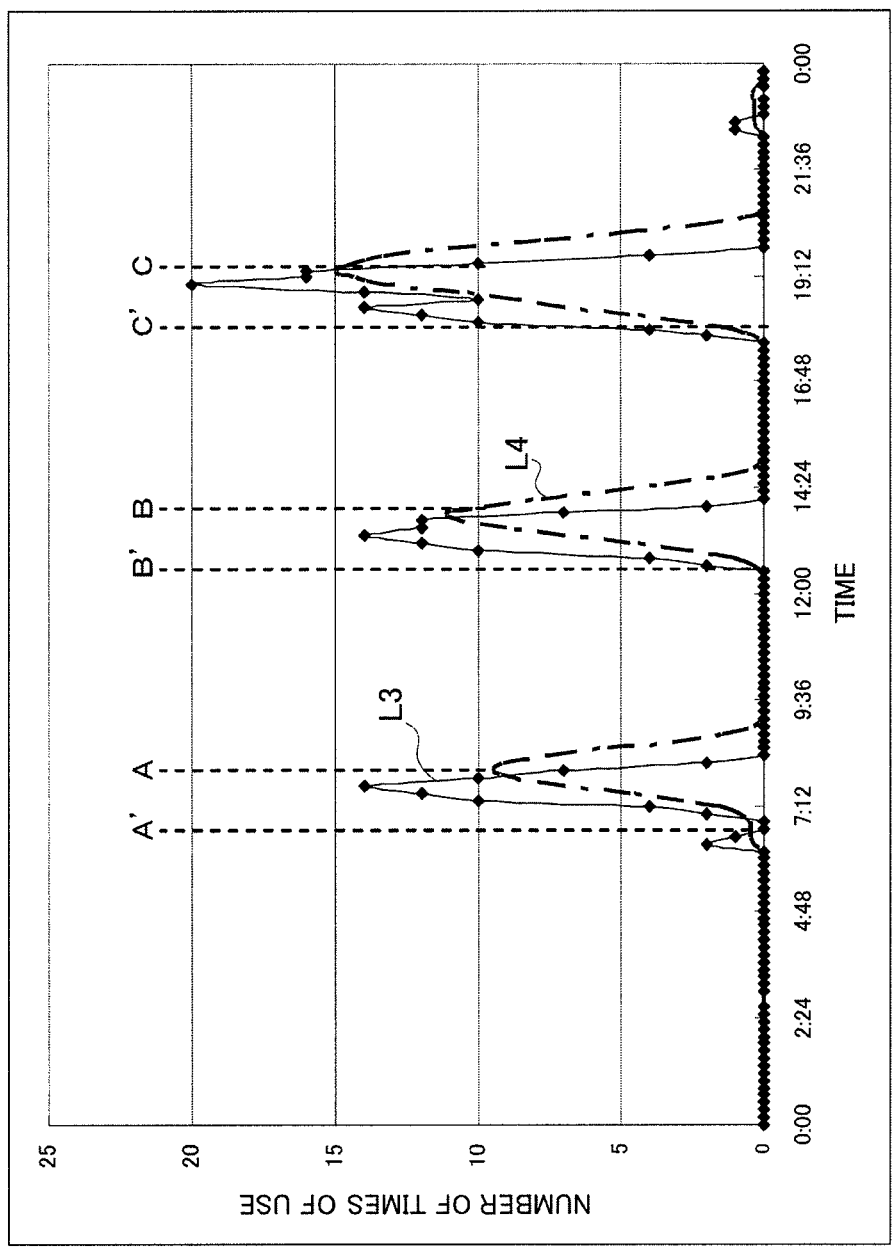
FIG. 9 is a drawing showing an exemplary table recording the number of times the patient uses the puncturing apparatus recorded in a recording section.

FIG. 9 is a drawing showing an exemplary table recording the number of times the patient uses the puncturing apparatus recorded in the recording section.

The table shown in FIG. 9 is a distribution map of the number of times the patient who performs puncturing operations three times per day uses the puncturing apparatus, and here, the number of times the patient uses the puncturing apparatus is recorded every ten minutes in the recording section.

As shown in a table in FIG. 9, graph L3, which shows a distribution of the number of times the patient uses the puncturing apparatus (the number of times of puncturing), indicates that the frequency of use is high after each meal because the patient performs puncturing after each meal. When a moving average of the distribution of this number of times the patient uses the puncturing apparatus (shown by graph L3 of the solid line), for example, the moving average per hour is calculated, the result is shown as graph L4 of the dashed line. Learning circuit section 284 estimates a peak point of dashed line L4 to be each time (A, B, C) this patient uses the puncturing apparatus, using this table. The timing to start preliminary charging is estimated at a predetermined time before each time (A, B and C) the patient uses the puncturing apparatus so as to have already completed the preliminary charging at the estimated time of use. For example, in FIG. 9, assuming that the timing to start preliminary charging is 2 hours before (the time indicated by each of A', B' and C') the time estimated by learning circuit section 284 (here, the preliminary charging takes about thirty seconds), the preliminary charging is already completed when the patient uses the puncturing apparatus (each time indicated by A, B and C). As described above, by starting preliminary charging at each of estimated timings A' B' and C', the period from when the preliminary charging is completed to each of times A, B, and C the patient uses the puncturing apparatus is not long, so that self-discharge of capacitor 25 becomes smaller.

Here, in a case in which puncturing is performed at the time the frequency of use is low, that is, puncturing is performed at an unusual time, the patient presses the switch of input section 29 to input, to control section 28, a signal indicating start of preliminary charging, that is, indicating "start by operation to prepare for puncturing by the patient" and thereby control section 28 starts preliminary charging.

Figure 10:
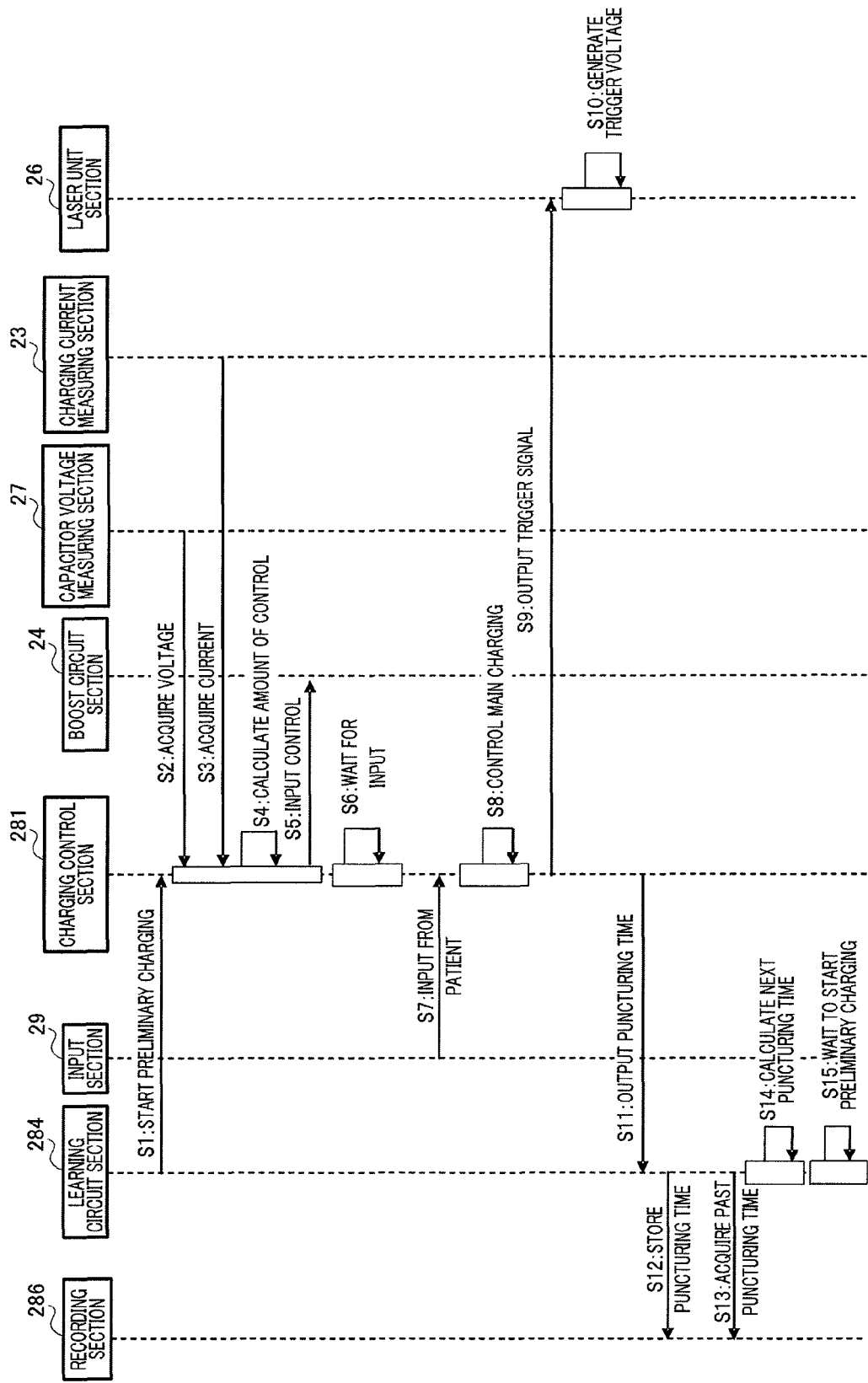
FIG. 10 is a sequence diagram explaining control when preliminary charging is started by a learning function.

FIG. 10 is a sequence diagram explaining control when preliminary charging is performed by a learning function. Here, explanation will be based on the assumption that the duration for which the patient uses the puncturing apparatus is sufficiently long and the learning function is operating, that is, preliminary charging is not performed through operation by the patient but is performed using data of the number of times the patient uses the puncturing apparatus (learning data), which is recorded in recording section 286.

The preliminary charging is started by a signal from learning circuit section 284 having the function described above.

As shown in FIG. 10, first, in step S1, learning circuit section 284 notifies charging control section 281 of an estimated preliminary charging starting timing, and when charging control section 281 receives this notification, charging control section 281 starts preliminary charging. To be more specific, two hours before the time at which the patient uses the puncturing apparatus, which is calculated based on past data, learning circuit section 284 outputs a preliminary charging start signal to charging control section 281.

In step S2, charging control section 281 to which the preliminary charging starting signal is inputted acquires the voltage of capacitor 25 from capacitor voltage measuring section 27.

Moreover, in step S3, charging control section 281 acquires the charging current from charging current measuring section 23, and the step moves to step S4.

In step S4, charging control section 281 calculates control signals such that the acquired charging current is 100 mA, and the step moves to step S5.

In step S5, charging control section 281 outputs the calculated control signal (boosted output control signal) to boost circuit section 24. By this means, charging to capacitor 25 is started through boost circuit section 24.

Here, charging control section 281 controls the processing from step S2 to step S5 while monitoring the voltage of capacitor 25 being equal to or lower than the preliminary charging voltage of 290 V based on the received signal as input from capacitor voltage measuring section 27.

Charging control section 281 controls boost control section 24 by input of the voltage of capacitor 25 indicating that the voltage of capacitor 25 has reached 290 V, stops the preliminary charging and waits for input from input section 29 in step S6.

That is, in step S6, charging control section 281 waits for input from the patient through input section 29 by which the patient operates input section 29.

In step S7, information indicating that puncturing is performed is inputted from the patient to input section 29 by pressing a pushing button and so forth, and then this input is inputted to charging control section 281.

In step S8, charging control section 281 acquires the voltage of capacitor 25 from capacitor voltage measuring section 27, acquires the charging current from charging current measuring section 23, calculates a control signal for main charging (boosted output control signal) based on those voltage and current and outputs the calculated result to boost circuit section 24. By this means, main charging to capacitor 25 is started through boost circuit section 24.

To be more specific, in step S8, charging control section 281 performs main charging control. In this step S8, charging control section 281 performs control to make the charging current 2 A and performs control repeatedly by calculating a control signal based on the inputted voltage of capacitor 25 and charging current and outputting the calculated control signal to boost circuit section 24 until the voltage of capacitor 25 reaches the main charging voltage of 400 V.

When the voltage of capacitor 25 reaches 400 V, charging control section 281 stops the charging to capacitor 25 performed through boost circuit section 24, and the step moves to step S9.

In step S9, charging control section 281 outputs a trigger signal to laser unit section 26.

In step S10, when the trigger signal is received as input, laser unit section 26 generates a trigger voltage to output laser light. By this means, the patient is punctured.

When the puncturing is completed, in step S11, charging control section 281 outputs the time at which this puncturing is performed to learning circuit section 284 and the step moves to step S12.

In step S12, learning circuit section 284 stores the time at this puncturing in recording section 286 and therefore the time of this puncturing is recorded in recording section 286, and the step moves to step S13.

In step S13, learning circuit section 284 acquires every past puncturing time stored in recording section 286, and the step moves to step S14.

In step S14, learning circuit section 284 statistically processes past puncturing times and calculates the time this patient performs puncturing the next time, that is, the time (timing) at which the preliminary charging is started for the next puncturing performed by this patient next, and the step moves to step S15.

In step S15, learning circuit section 284 waits until two hours before the next puncturing time, that is, until preliminary charging is started, using a signal from timer 282 inputted through charging control section 281.

Thus, the everyday puncturing time of the patient is recorded using learning circuit section 284 and preliminary charging to capacitor 25 is started a predetermined time before the puncturing time, so that the preliminary charging is not performed immediately after the puncturing. By this means, the power loss caused by self-discharge of capacitor 25 after preliminary charging occurs only at the time before the predetermined period from the puncturing time. Therefore, even if the frequency at which the patient uses the puncturing apparatus is low, the loss caused by self-discharge of capacitor 25 can be prevented by a relatively simple configuration, as compared with capacitor 25 in which preliminary charging is performed immediately after the puncturing and then the next puncturing is not performed.

Here, when there is no data to be learned (data indicating the number of times the patient uses the puncturing apparatus everyday) in recording section 286, the case of "start of preliminary charging by the patient" is adopted, and preferably, the learning function is executed by the learning function section when the predetermined amount of learning data is accumulated in recording section 286.

Here, "start of preliminary charging by the patient" will be described.

In this case, preliminary charging is started in conjunction with preparation operation, which the patient performs when using the puncturing apparatus having high-voltage generating circuit 21.

To be more specific, for example, a puncturing protective cover is provided in the laser emitting section (puncturing section) of laser unit section 26 in puncturing apparatus 20, and a detecting means (e.g., switch) for detecting the protective cover being open or closed is also provided in puncturing apparatus 20. An output signal from this detecting means is inputted to control section 28 (to be more specific, charging control section 281), and when this input signal is received as input, control section 28 starts preliminary charging. By this means, when the patient opens (removes) this protective cover for performing puncturing, preliminary charging is started.

In addition, for example, when the puncturing apparatus is not used, the puncturing apparatus having high-voltage generating circuit 21 may be placed in a sleep mode (the system operates in a low power consumption state), whereas while the puncturing apparatus is in use, the sleep mode may be canceled at the time the patient presses the operation button of input section 29 and input from the patient to perform puncturing may be waited.

In this case, control section 28 controls the entire high-voltage generating circuit 21 in a power-saving mode after outputting a trigger signal to laser unit section 26, and when a signal indicating start of preliminary charging is received from input section 29 as input, control section 28 controls the entire system including boost circuit section 24. In addition, control section 28 waits until a signal indicating start of main charging, that is, a signal indicating a puncturing command, is inputted from input section 29 in a state where control section receives a signal indicating start of preliminary charging as input. When receiving this signal indicating start of main charging, control section 28 controls boost circuit section 24 to perform main charging to capacitor 25. Here, preliminary charging in the puncturing apparatus may be set to be started at the same time as the sleep mode of the system is canceled. In this case, it is assumed that the preliminary charging started in the preparation operation has not been completed until the patient performs puncturing. In this case, control section 28 controls boost circuit section 24 to start main charging even if preliminary charging is being performed. In this configuration, although both the time the patient waits and the power loss until puncturing increase as before, data of the number of times the puncturing apparatus is used, which is recorded in recording section 28b, increases, so that this problem can be solved.

As described above, in the configuration in which the patient performs preliminary charging, that is "starting by the patient to prepare for puncturing", charging to capacitor 25 can be reliably performed at a timing not too early.

Here, a case in which "puncturing is performed through operation by the patient after preliminary charging" will be described.

Figure 11:
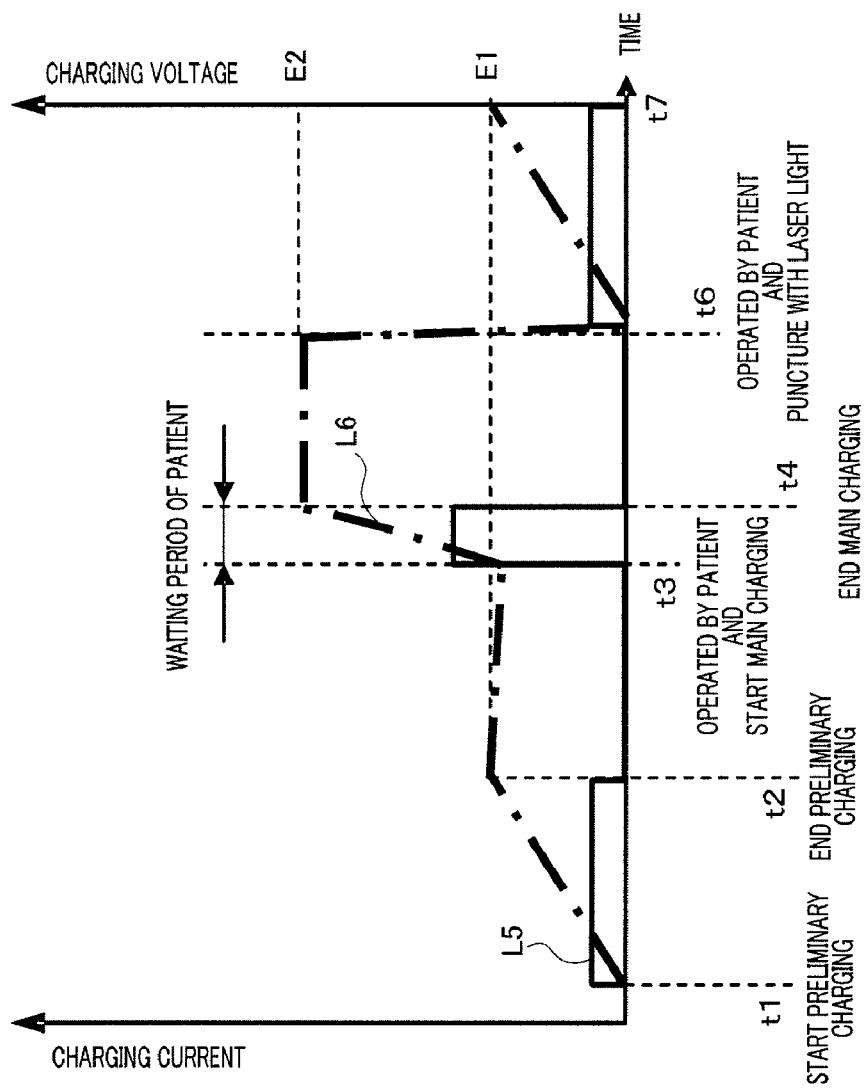
FIG. 11 is an operation timing chart explaining operations of the high-voltage generating circuit when the patient operates the puncturing apparatus to perform puncturing after preliminary charging.

FIG. 11 is an operation timing chart explaining operations of high-voltage generating circuit 21 when puncturing is performed through operation by the patient after preliminary charging. In FIG. 11, the horizontal axis shows time, the vertical axis shows the magnitude of a charging voltage and a charging current, solid line L5 shows a charging current and dashed line L6 shows a charging voltage.

In the puncturing apparatus having the high-voltage generating circuit, control in the case in which "puncturing is performed through operation by the patient after preliminary charging" is different from the control in the case in which "puncturing is performed immediately after main charging" in that operation by the patient after main charging (time t4) is waited for again. Here, the control until t4 after completion of the main charging is the same as in FIG. 7 and is performed at the same timing as in FIG. 7, so that descriptions will be omitted.

After completion of the main charging (time t4), the system waits for again input from patient. That is, control section 28 monitors the voltage across capacitor 25 using capacitor voltage measuring section 27, in the same manner as in preliminary charging while controlling boost circuit section 24. When the voltage of capacitor 25 becomes the main charging voltage E2 (e.g., 400V), which is the puncturing laser oscillation voltage in the present embodiment, control section 28 waits until input section 29 inputs a signal indicating a command to emit laser light (until time t4 to time t6).

When the patient presses again a puncturing button and so forth of input section 29 at a preferred timing, a signal commanding to emit laser light (laser puncturing command) is inputted from input section 29 to control section 28 at time t6. When receiving this signal, control section 28 outputs a trigger signal to laser unit 26 to make laser unit section 26 emit laser light to puncture skin. In FIG. 11, "operation by the patient to command to emit laser light" and "laser puncturing" operation are performed at time t6. At the time t6, when laser puncturing is finished, the voltage of capacitor 25 becomes 0, and control section 28 controls boost circuit section 24 to start preliminary charging to capacitor 25 again.

As described above, in puncturing apparatus 20, laser light is emitted at the same time as the patient presses the puncturing button of input section 29. Therefore, the patient can perform puncturing at the timing the patient wants to do.

However, if a state in which the main charging has been completed continues for a predetermined time (e.g., one minute), it is necessary to reduce again the charging voltage to equal to or lower than the laser oscillation level to assure safety. In this case, the charging voltage will be reduced by regenerating electric power in capacitor 25 or discharging capacitor 25.

Now, in the puncturing apparatus having high-voltage generating circuit 21, a configuration will be described as embodiment 2 where a voltage is regenerated in capacitor 25 in which the main charging has been performed.

(Embodiment 2)

Figure 12:
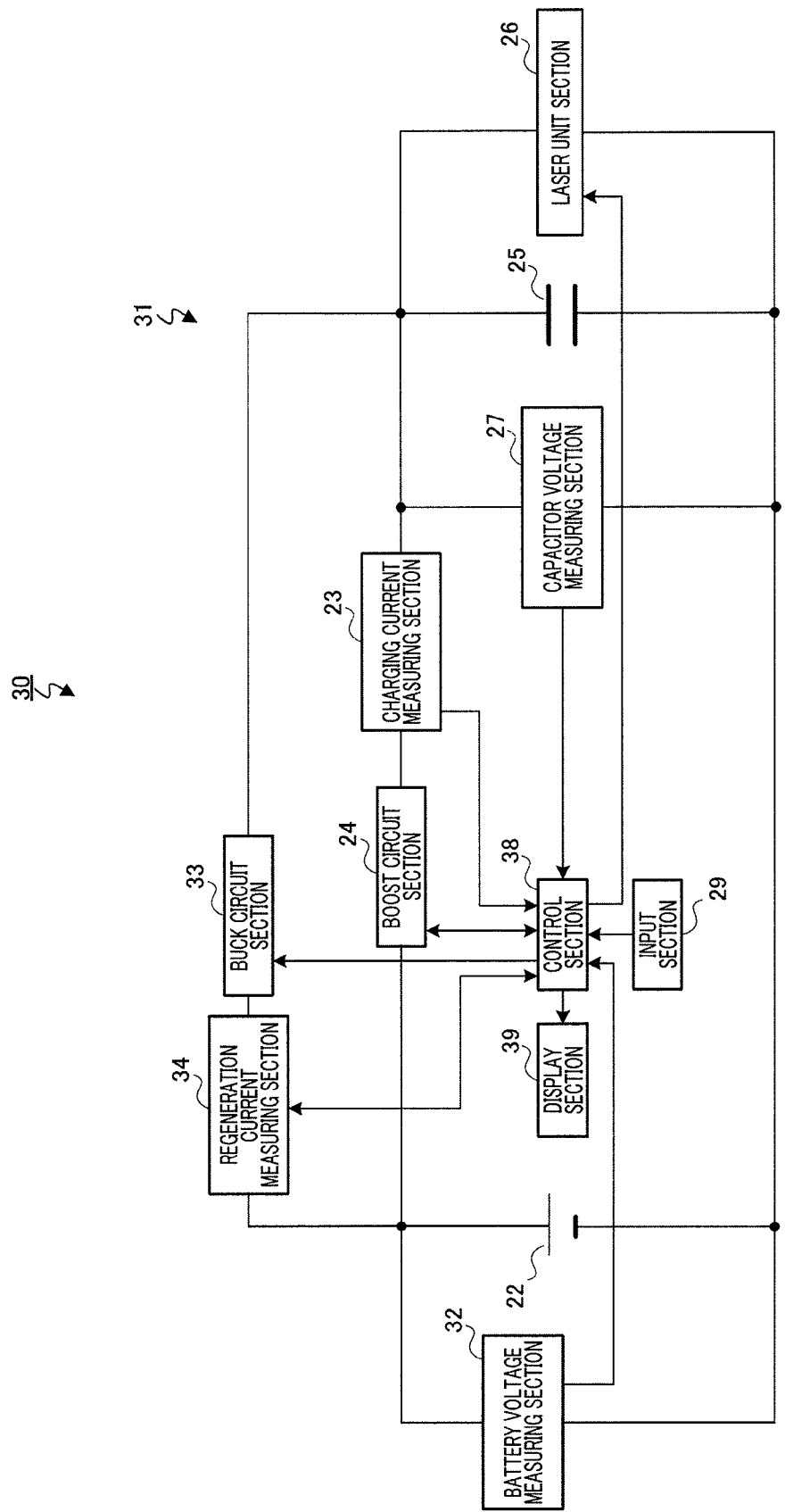
FIG. 12 is a block diagram showing a configuration of primary parts of a puncturing apparatus having a high-voltage generating circuit according to embodiment 2 of the present invention.

FIG. 12 is a block diagram showing a configuration of primary parts of puncturing apparatus 30 having high-voltage generating circuit 31 according to embodiment 2 of the present invention.

Puncturing apparatus 30 shown in FIG. 12 has the same basic configuration as that of puncturing apparatus 20, which includes battery voltage measuring section 32, buck circuit section 33 and regeneration current measuring section 34 in addition to the configuration of puncturing apparatus 20. Therefore, the same names and reference numerals will be assigned to the same components and descriptions will be omitted.

In puncturing apparatus 30 shown in FIG. 12, the input of high-voltage generating circuit 31 is connected to battery 22 and the output is connected to laser puncturing apparatus 26.

High-voltage generating circuit 31 has a regenerating function for returning the voltage of capacitor 25 to battery 22 in addition to the function of high-voltage generating circuit 21.

Here, battery 22 is configured by a secondary battery such as a lithium-ion secondary battery, for example.

To be more specific, high-voltage generating circuit 31 has battery voltage measuring section 32, buck circuit section 33 and regeneration current measuring section 34 for providing the regenerating function, in addition to boost circuit 24, charging current measuring section (hereinafter referred to as "current measuring section") 23, capacitor 25, capacitor voltage measuring section (hereinafter referred to as "voltage measuring section") 27, control section 38, input section 29 and display section 39.

Battery voltage measuring section 32 is connected to both ends of battery 22, measures the voltage of battery 22 and outputs the measurement result to control section 38.

Buck circuit section 33 is connected to capacitor 25, reduces the high voltage charged in capacitor 25 to 3 to 5 V and outputs the voltage to battery 22 through regeneration current measuring section 34.

Regeneration current measuring section 34 measures the regeneration current outputted from capacitor 25 to battery 22 and outputs the measurement result to control section 38.

Control section 38 performs regeneration control based on the input from regeneration current measuring section 34 and battery voltage measuring section 32.

Figure 13:
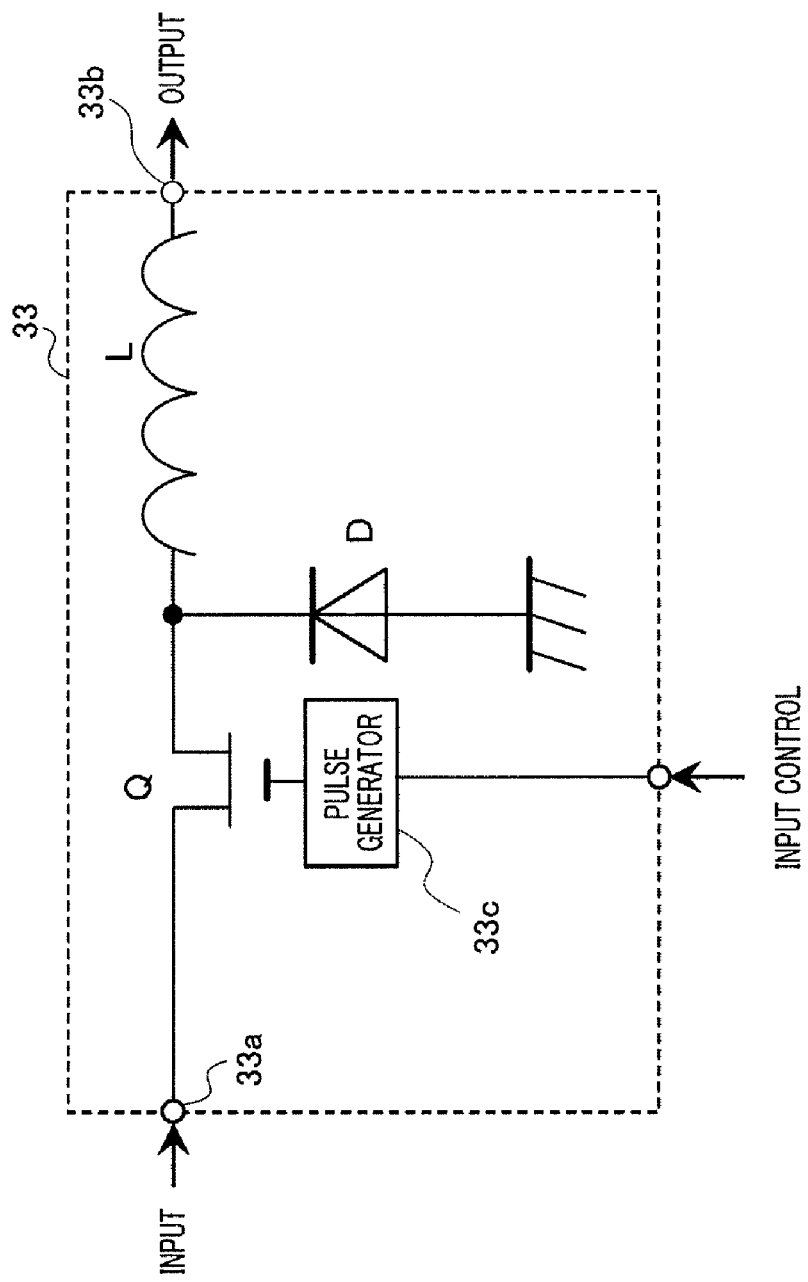
FIG. 13 is a block diagram showing an exemplary configuration of a buck circuit section.
Figure 14:
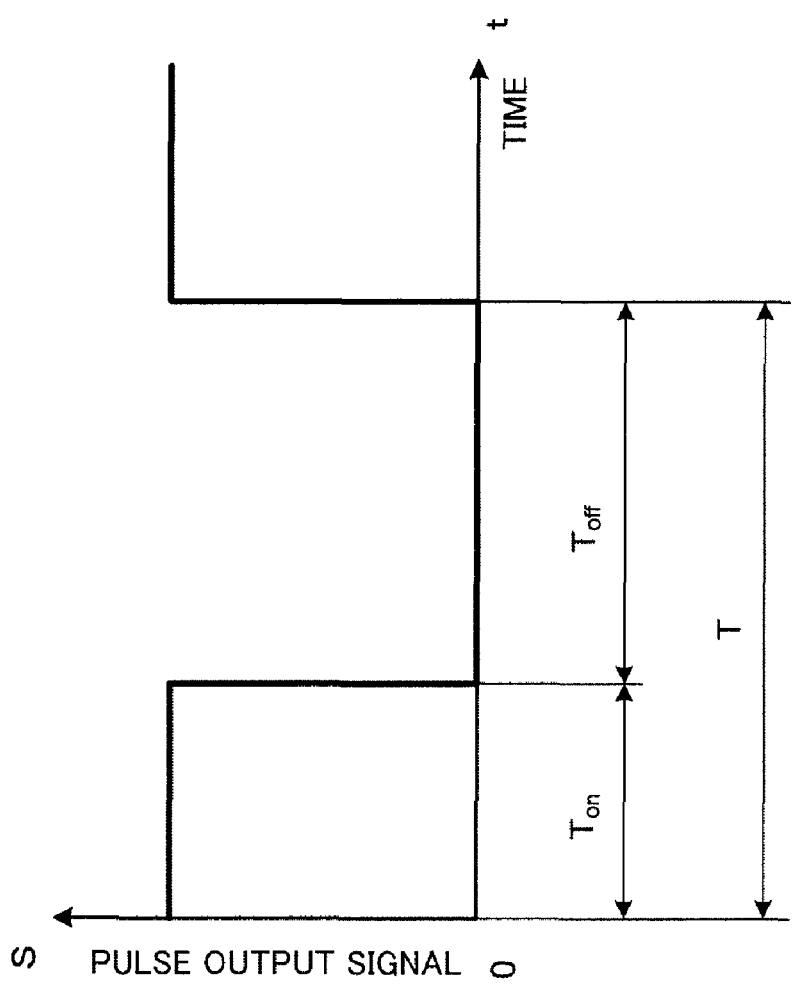
FIG. 14 is a drawing showing a pulse waveform outputted from a pulse generator shown in FIG. 13.

FIG. 13 is a block diagram showing an exemplary configuration of buck circuit section 33 and FIG. 14 is a drawing showing a pulse waveform outputted from a pulse generator shown in FIG. 13.

Buck circuit section 33 reduces the inputted voltage and outputs the result, and here, a buck chopper circuit is used as buck circuit section 33. Buck circuit section 33 according to the present embodiment reduces the inputted voltage of 200 to 700 V to 3 to 5 V and outputs the reduced voltage. In buck circuit section 33, the voltage of capacitor 25 is inputted to switching transistor Q connected to one end of capacitor 25 through input section 33a. Pulse generator 33c is connected to a switching input of this switching transistor Q, current smoothing reactance L and flyback diode D are connected to the other end (output side) of switching transistor Q.

In addition, the other end of reactance L is connected to output section 33b, the voltage reduced in buck circuit section 33 is outputted from output section 33b.

Pulse generator 33c is connected to external control section 38, and receives a control input signal from control section 38 as input.

When receiving the control input signal, pulse generator 33c generates a pulse wave that changes the proportion of on-time Ton at a predetermined period (1 kHz to 40 kHz) as shown in FIG. 14. The output voltage or current of buck circuit section 33 can be changed through switching transistor Q in accordance with this proportion of the on-time.

Figure 15:
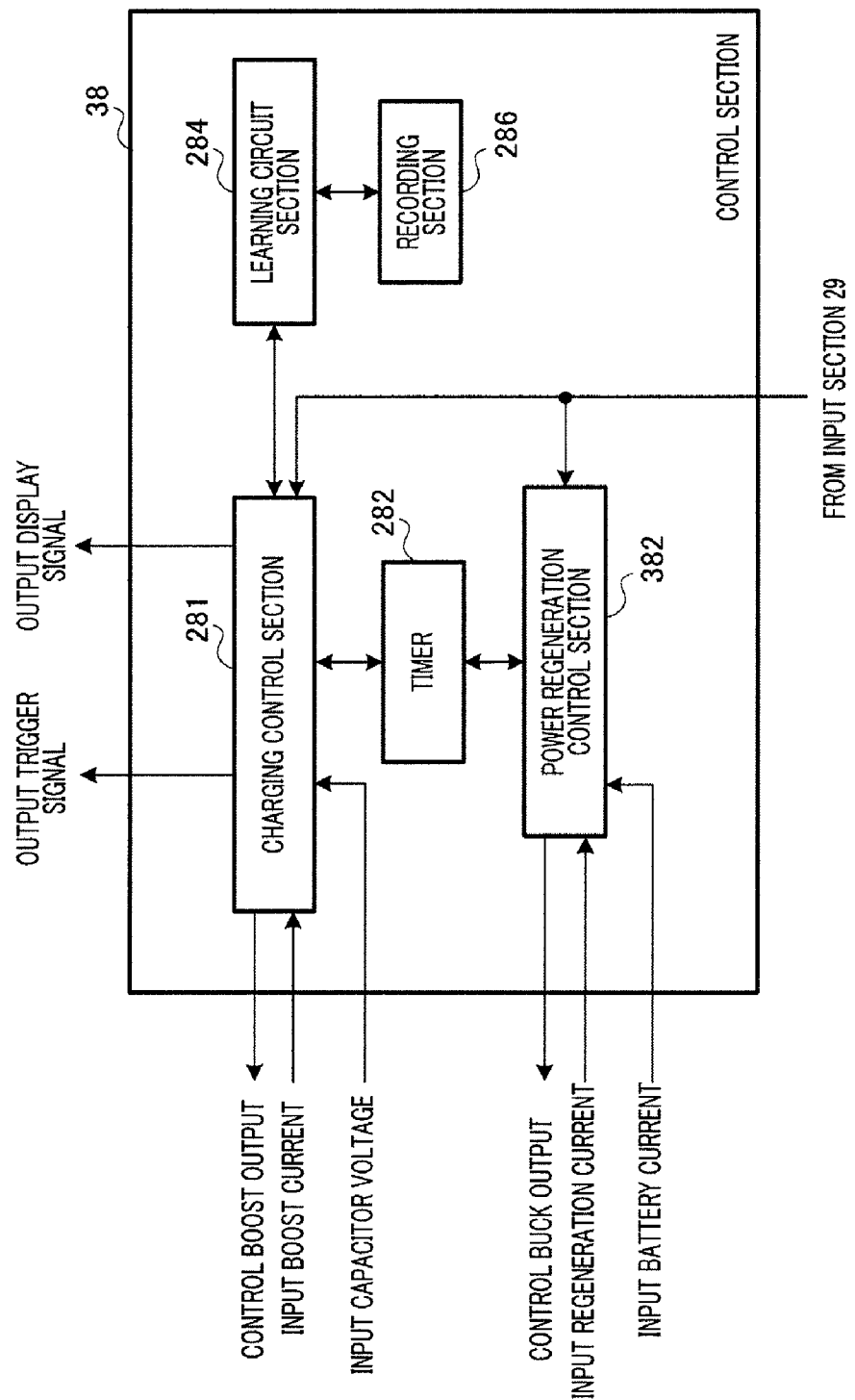
FIG. 15 is a functional block diagram showing a configuration of a control section.

FIG. 15 is a functional block diagram showing a configuration of control section 38. Here, control section 38 has the same basic configuration as that of control section 28 according to embodiment 1 described above. Therefore, the same components as in control section 28 will be assigned the same names and reference numerals and detailed descriptions will be omitted.

Control section 38 has power regeneration control section 382 connected to timer 282, in addition to charging control section 281, timer 282, learning circuit section 284 and recording section 286.

That is, in control section 38, timer 282 measures the time of the system in puncturing apparatus 30 and outputs the result to charging control section 282 and electric power regeneration control section 282 connected to control section 38.

Charging control section 281 determines the time to start preliminary charging using the input signal from timer 282, indicating the time. In addition, charging control section 281 outputs a trigger signal for emitting laser light to laser unit section 26 and also outputs the time to output the trigger signal to learning circuit section 284.

In addition, learning circuit section 284 stores the time to output the inputted trigger signal in recording section 286 and estimates the time the patient uses the puncturing apparatus based on past data as described above (see FIG. 8). Then, a predetermined time before the time the patient uses the puncturing apparatus, learning circuit section 284 outputs this fact to charging control section 281, and when receiving this signal, charging control section 281 controls boost circuit section 24 to start preliminary charging to capacitor 25.

Power regeneration control section 382 is connected to battery voltage measuring section 32, buck circuit section 33, line current measuring section 34 and input section 29 outside control section 38, and performs power regeneration control using buck circuit section 33 based on the signal received as input. In addition, when receiving the input from timer 282, power regeneration section 382 judges whether or not timeout occurs after completion of main charging and starts power regeneration control when the timeout occurs.

To be more specific, power regeneration section 382 outputs a control signal to command buck circuit section 33 based on the battery voltage obtained from battery voltage measuring section 32 and regeneration current measuring section connected to power regeneration control section 382 and a signal indicating the regeneration current.

By this means, power regeneration control section 382 controls the output of buck circuit section 33 to be an arbitrary voltage or current and performs the optimum charging control for the battery characteristic of battery 22 (here, a secondary battery).

Here, battery 22 is a lithium-ion secondary battery. General charging control corresponding to the lithium-ion battery characteristic is constant current control when the voltage of battery 22 is lower than 3.7 V, and is constant voltage control at 3.7 V when the voltage of battery 22 reaches 3.7 V.

Therefore, with charging control (regeneration control) in control section 38, power regeneration control section 382 performs constant current control of buck circuit section 33 using the input of regeneration current measuring section 34 in order to prevent the current value from being more than, for example, 100 mA when the battery voltage value is lower than 3.7 V.

In addition, when the battery voltage value reaches 3.7 V, power regeneration control section 382 performs constant voltage control of buck circuit section 33 using the input of regeneration voltage measuring section 34 in order to prevent the battery voltage value from being higher than 3.7 V. At this time, it takes about thirty seconds from the main charging voltage: 400 V to the preliminary charging voltage: 290 V and further takes about thirty seconds to regenerate capacitor 25 until the charging voltage is completely 0. However, when the remaining amount of battery 22 is large and the battery voltage is 3.7 V, it may take a longer time to reduce the regeneration current.

As described above, power regeneration control section 382 can arbitrarily control the current value and the voltage value for battery 22 by outputting the control signal to buck circuit section 33 and performs appropriate charging control of battery 22 by the known technology even if the kind of battery 22, which is a secondary battery, is changed.

By this means, in the case in which "puncturing is performed through operation by the patient after preliminary charging" in puncturing apparatus 20 according to embodiment 1, when the operation by the patient through input section 29 (e.g., the operation to press the puncturing switch of input section 29) is not performed for equal to or more than a predetermined period (e.g., one minute), the system (power regeneration control section 382 in control section 38) of puncturing apparatus 30 performs power regeneration operation, including detecting timeout using timer 282 and controlling buck circuit section 33 to reduce the charging voltage of capacitor 25 to equal to or lower than the laser oscillation level or 0. Otherwise, charging control section 281 performs forcible discharge. By this means, a state in which a high-charging voltage is held in capacitor 25 for a long time can be prevented and the risk of emitting laser light from laser unit section 26 as a result of an erroneous operation.

Figure 16:
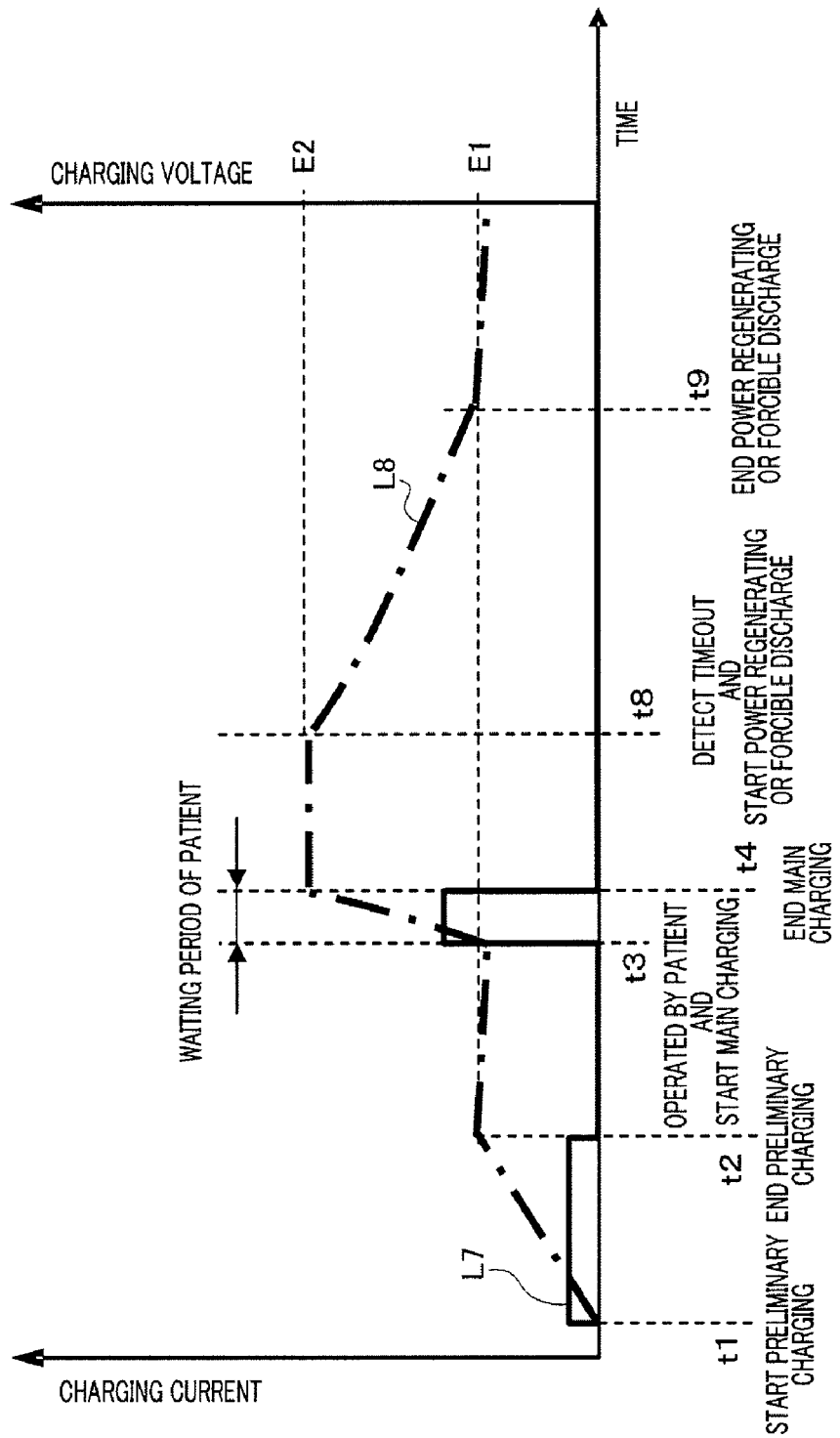
FIG. 16 is an operation timing chart explaining operations of the high-voltage generating circuit according to embodiment 2 of the present invention.

FIG. 16 is an operation timing chart explaining operations of high-voltage generating circuit 31 according to embodiment 2 of the present invention. In FIG. 16, the horizontal axis shows time, the vertical axis shows the magnitude of the charging voltage and the charging current, solid line L7 shows the charging current and dashed line L6 shows the charging voltage. Here, control until t4 after completion of main charging in puncturing apparatus 30 is the same as in FIG. 7 and FIG. 11 and is performed at the same timing as in FIG. 7 and FIG. 11, so that descriptions will be omitted.

After completion of main charging (time t4), the system waits for again input from patient. After completion of main charging, the system starts measuring a period of time, and when the period of time is over a predetermined period of time and therefore timeout is detected, the system starts regenerating power using buck circuit section 33 or forcible discharge using resistance.

To be more specific, in control section 38, timer 282 starts measuring a period of time while charging control section 281 and power regeneration section 382 wait for input from input section 29.

When power regeneration is performed, power regeneration control section 382 detects timeout when there is no input from input section 29 and the period of time measured by power regeneration control section is over a predetermined period of time, and starts regenerating power using buck circuit section 33.

On the other hand, when forcible discharge is performed, charging control section 281 detects timeout when there is no input from input section 29 and the period of time measured by timer 282 is over a predetermined period of time. Then, charging control section 281 controls a switching element (not shown) such as a transistor and connects capacitor 25 to a resistance (not shown) connected parallel to capacitor 25 to consume the charging power in the resistance. By this means, the charging voltage of capacitor 25 is reduced.

After that, the system (charging control section 281 or power regeneration control section 382) monitors the voltage of capacitor 25 using the measurement result of capacitor voltage measuring section 27, and when the voltage of capacitor 25 is equal to or lower than the laser oscillation level E1, the system stops the power regeneration or forcible discharge and waits for again operation of main charging by the patient (the input signal indicating start of main charging from input section 29).

At this time, when the start timing of preliminary charging is determined using learning circuit section 284, or when preliminary charging is started based on a preliminary charging start factor, it is desired that power regeneration or forcible discharge is performed until the amount of charge to capacitor 25 becomes 0. In this case, the system waits for start of preliminary charging.

Here, when forcible discharge is performed, since the charged power is discharged, power is consumed without emitting laser light. On the other hand, when power regeneration is performed, since the power charged in capacitor 25 is returned to the secondary battery, power consumption can be minimized. By this means, even if the patient is placed in a state not allowing charge to the system, for example, the patient is not at home, a predetermined number of times of laser puncturing operations can be performed.

Figure 17:
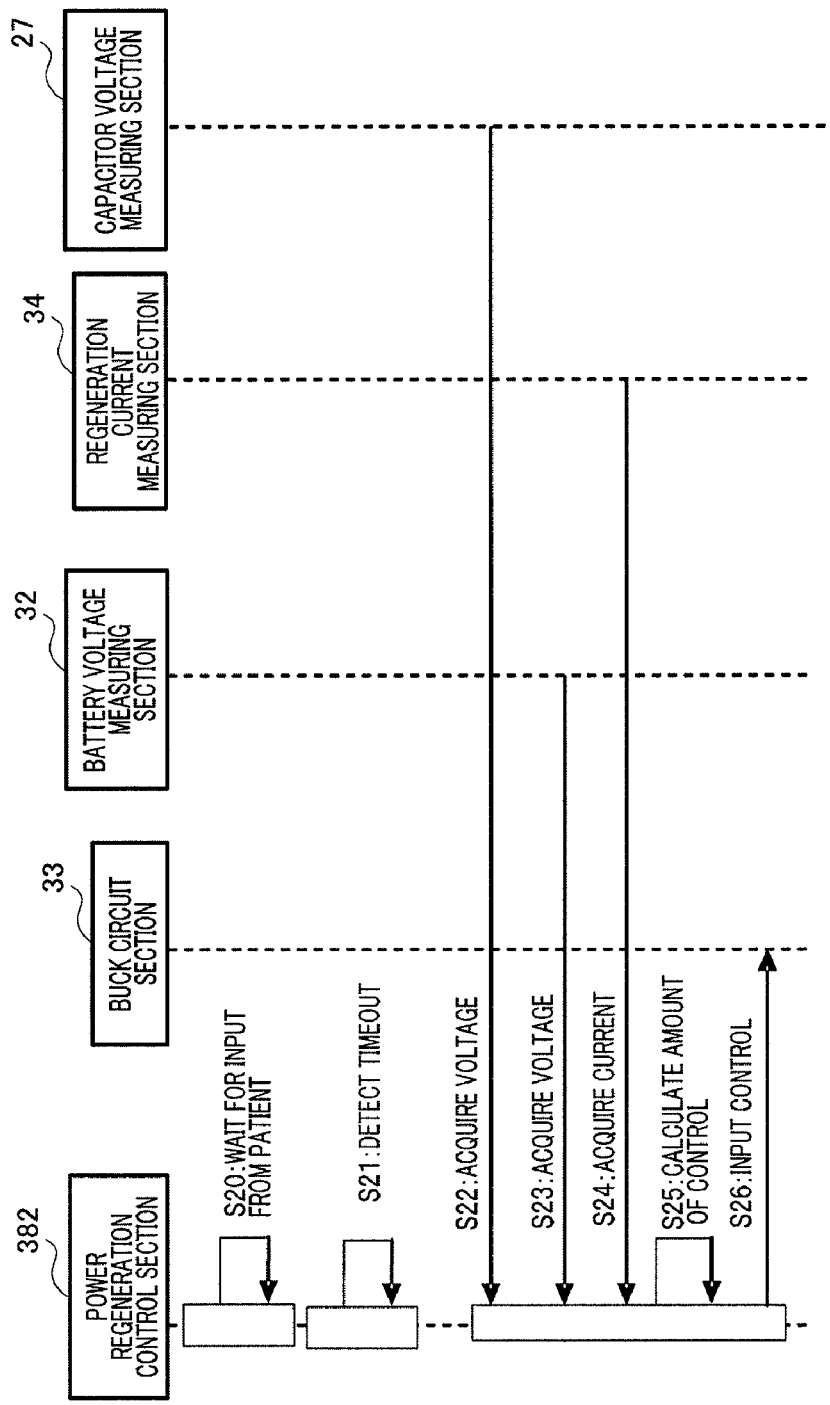
FIG. 17 is a sequence diagram explaining operations of an electric power regeneration control section.

FIG. 17 is a sequence diagram explaining operations of power regeneration control section 382.

Here, the operation of power regeneration control section 382 after main charging has been completed. Here, operation of puncturing apparatus 30 until main charging is performed is the same as the processing up to step S8 in FIG. 10. Therefore, the processing shown in FIG. 17 is processing after the main charging has been completed and after step S8, power regeneration control section 382 waits until detecting input from the patient, through a pushing button, indicating that puncturing is performed in step S20.

When this waiting period is over a predetermined period of time, for example, over one minute, power regeneration control section 382 to which a time measuring signal is inputted from timer 282 detects timeout in step S21. The purpose for this is to reduce the risk of emitting laser light by erroneous operation as a result of continuing a state in which a high voltage is charged (main charging state) in capacitor 25 for a long time.

In step 21, when detecting the timeout, power regeneration control section 382 controls buck circuit section 33 to start power regeneration operation.

In step S22, power regeneration control section 382 acquires the voltage of capacitor 25 from capacitor voltage measuring section 27. Here, the purpose for this is to monitor the voltage of capacitor 25 being equal to or lower than the preliminary charging voltage.

Further, in step S23, power regeneration control section 382 acquires a voltage of battery 22 from battery voltage measuring section 32 and in step S24, power regeneration control section 382 acquires a regeneration current from regeneration current measuring section 34.

In step S25, power regeneration control section 382 calculates the amount of control of buck circuit section 33 such that the appropriate regeneration control (charging control) is performed in the secondary battery (e.g., lithium-ion secondary battery) connected.

In step S26, power regeneration control section 382 outputs the amount of control of the voltage to be reduced, to buck circuit section 33. By this means, buck circuit section 33 can charge battery 22 with the current and voltage of the appropriate values.

Power can be regenerated by repeating the processing from step S22 to step S26 described above. When the voltage of the capacitor is lower than the preliminary charging voltage, the power regeneration section stops the processing from step 22 to step S26 and is placed in a waiting state.

As described above, in the present embodiment, in a state where main charging is performed in capacitor 25 and laser unit section 26 can perform laser oscillation, the power of capacitor 25 is reduced to preliminary charging voltage E1, which is the voltage equal to or lower than the laser oscillation level.

By this means, even if the patient forgets to start laser puncturing for example, it is possible to prevent the state in which a high charging voltage is held in capacitor 25 for a long time and it is possible to prevent laser unit section 26 from emitting laser light by erroneous operation.

(Embodiment 3)

Figure 18:
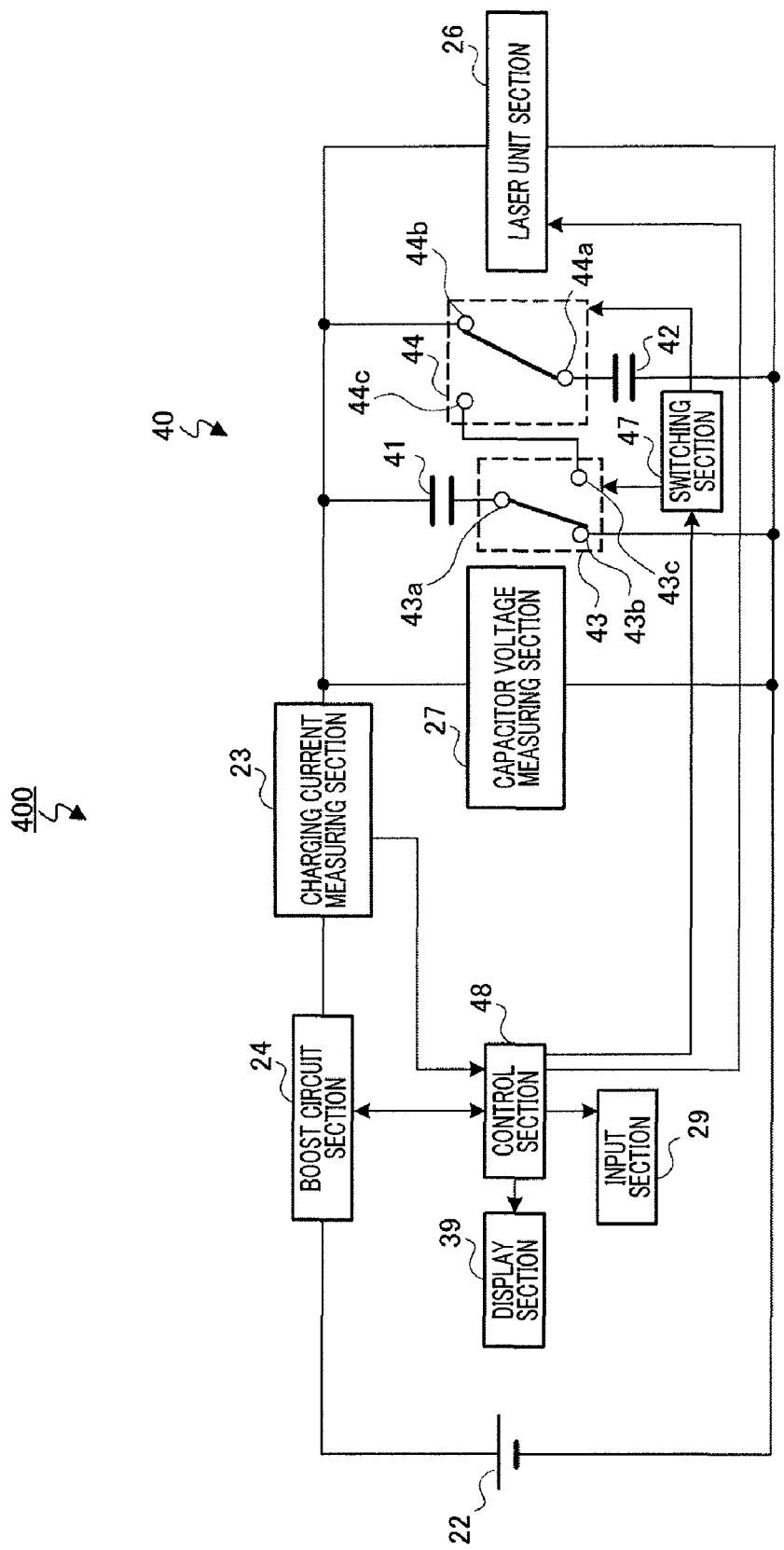
FIG. 18 is a block diagram showing a configuration of primary parts of a puncturing apparatus having a high-voltage generating circuit according to embodiment 3 of the present invention.

FIG. 18 is a block diagram showing a configuration of primary parts of puncturing apparatus 400 having high-voltage generating circuit 400 according to embodiment 3 of the present invention.

Here, high-voltage generating circuit 40 described in embodiment 3 has a configuration in which a plurality of capacitors, which serve the power supply for laser unit section 26, as compared with high-voltage generating circuit 21 according to embodiment 1.

To be more specific, high-voltage generating circuit 40 differs from high-voltage generating circuit 21 in that two (one or more) capacitors 41 and 42 are employed instead of one capacitor 25 employed in high-voltage generating circuit 21 according to embodiment 1, and these capacitors 41 and 42 are switched to be connected in series or in parallel. That is, high-voltage generating circuit 40 has changeover switches 43 and 44 configured by mechanical relays, transistors and so forth, which are connected to allow the connecting state of at least two or more connected capacitors 41 and 42 to be switched between parallel connection and serial connection, and switching section 47 that switches the changeover switches. The other aspects of high-voltage generating circuit 30 are substantially the same as those in embodiment 1, so that only differences will be explained, and the same components will be assigned the same names and reference numerals and descriptions will be omitted.

The input of high-voltage generating circuit 40 is connected to battery 22 and the output is connected to laser unit section 26.

High-voltage generating circuit 40 has boost circuit section 24, charging current measuring section (hereinafter referred to as "current measuring section") 23, capacitor voltage measuring section (hereinafter referred to as "voltage measuring section") 27, input section 29, display section 39, capacitors 41 and 42, changeover switches 43 and 44, switching section 47 and control section 48.

In high-voltage generating circuit 40 shown in FIG. 18, the positive terminal of capacitor 41 is connected to the output side of boost circuit 24 through charging current measuring section 23, and common terminal 43a of changeover terminal 43 is connected to the negative terminal of capacitor 41.

One terminal 43b of changeover switch 43 is connected to the negative side of battery 22 and the other terminal 43c is connected to the other terminal 44c of changeover switch 44.

In addition, one terminal 44b of changeover switch 44 is connected to the positive terminal of capacitor 42, and common terminal 44a of this changeover switch 44 is the positive terminal of capacitor 42. The negative terminal of capacitor 42 is connected to the negative side of battery 22.

Both ends of those capacitors 41 and 42 are connected to both ends of laser unit section 26, respectively.

Here, as both capacitor 41 and 42, capacitors having the same electrostatic capacity of 600 µF are used, and as both changeover switches, IGBTs are used. Here, changeover switches 43 and 44 are not limited to IGBTs, and mechanical relays, FETs and so forth, which can electrically changeover the state of switches, may be employed.

Switching section 47 is connected to control section 48, and changeover switches 43 and 44. Switching section 47 switches between changeover switches 43 and 44 such that capacitors 41 and 42 are connected in series or parallel by a switching signal inputted from control section 48.

Figure 19:
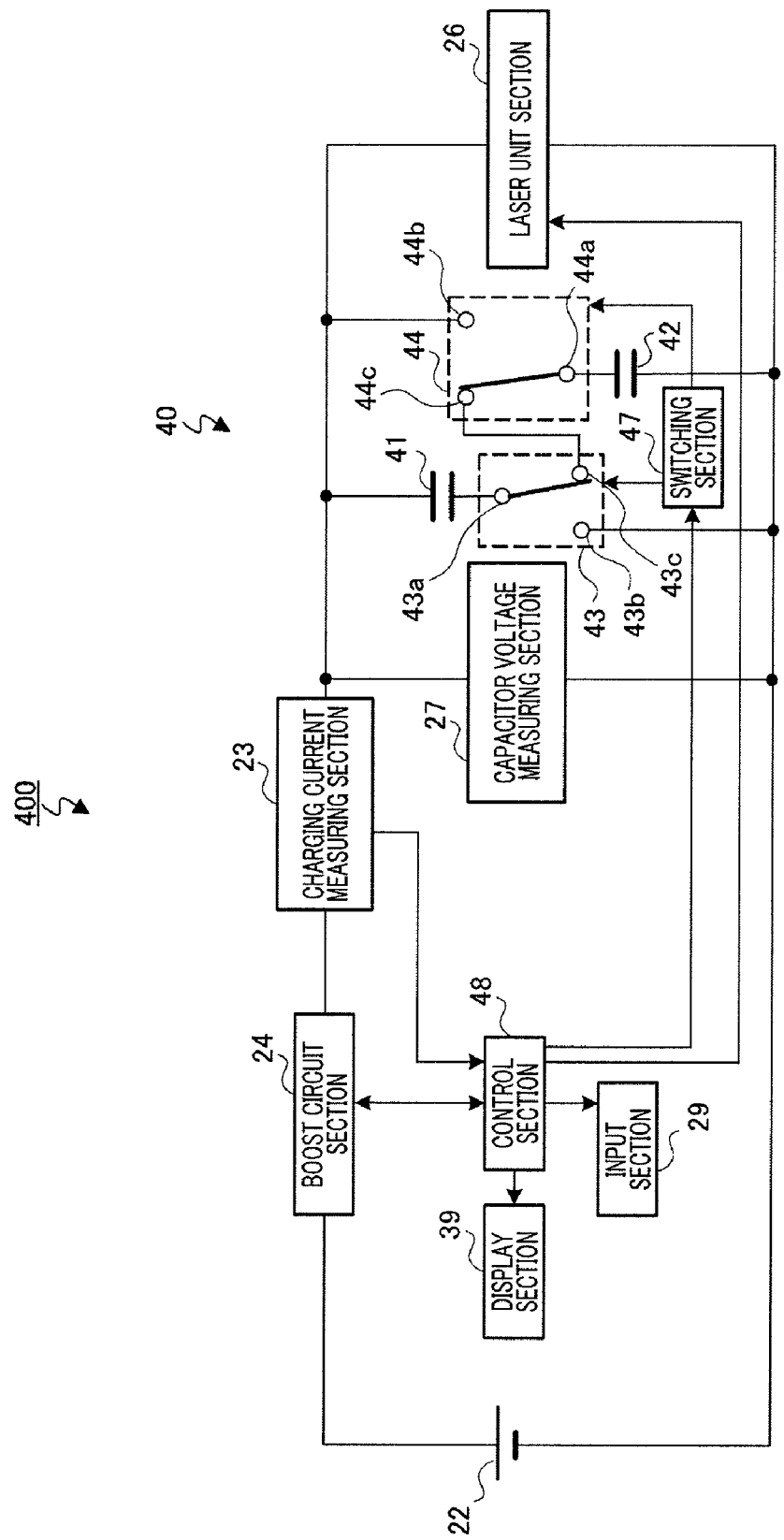
FIG. 19 is a block diagram showing a state in which capacitors are connected in series by changeover switches in the puncturing apparatus shown in FIG. 18.

FIG. 19 is a block diagram showing a state in which capacitors 41 and 42 are connected in series by changeover switches 43 and 44.

Control section 48 has functions to output a switching signal to switching section 47 based on the signal received as input and connect capacitors 41 and 42 in parallel or series, in addition to the same functions as those of control section 28.

Figure 20:
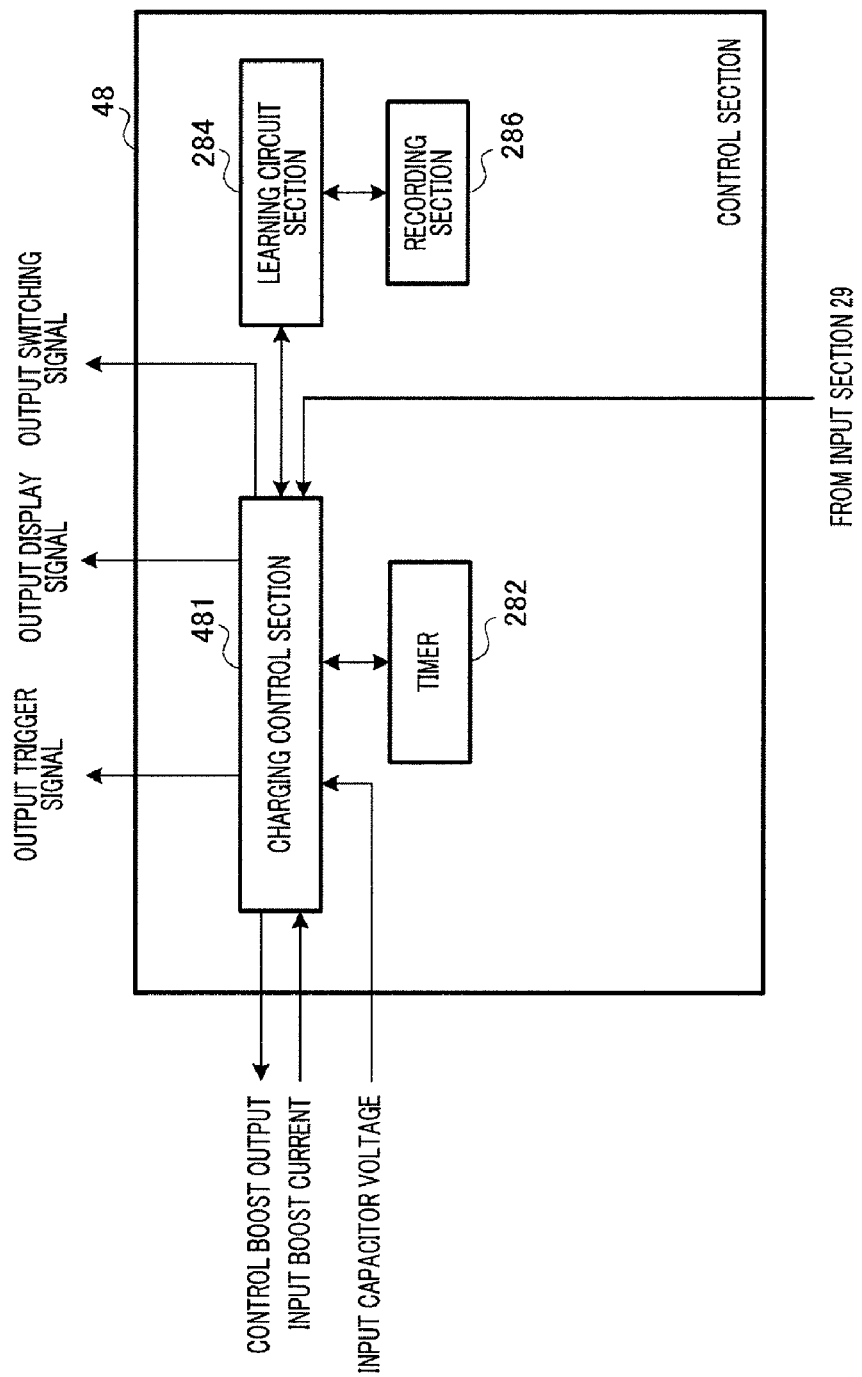
FIG. 20 is a functional block diagram showing a configuration of the control section.

FIG. 20 is a functional block diagram showing a configuration of control section 48. As shown in FIG. 19, control section has the same configuration as that of control section 28 except control section 48 outputs a switching signal to control the charging voltage, so that description will be omitted.

To be more specific, charging control section 281 has charging control section 481, timer 282, learning circuit section 284 and recording section 286.

Charging current measuring section 23, boost circuit section 24, capacitor voltage measuring section 27, input section 29, display section 39 and switching section 47 are connected to charging control section 481.

A boosted output current from charging current measuring section 23, a capacitor voltage from capacitor voltage measuring section 27 and a signal from input section 29, indicating start of puncturing by the patient, are inputted to charging control section 481. In addition, the time from timer 282, timing information of the preliminary charging from learning circuit section and so forth are inputted to charging control section 481.

Charging control section 481 outputs a control signal to control the boosted output of boost circuit section 24 to boost circuit section 24, outputs a trigger signal to make laser unit section 26 emit laser light to laser unit section 26, outputs display information to display section 39 and outputs a switching signal to switching section 47. Here, charging control section 481 outputs a trigger signal output time to learning circuit section 284 to make learning circuit section 284 estimate the preliminary charging starting timing in accordance with the time the patient uses the puncturing apparatus.

When receiving information as input, indicating the start of preliminary charging by the patient from input section 29, and indicating the timing to start preliminary charging from learning circuit section 284, or indicating a predetermined timing to start preliminary charging, and so forth, charging control section 481 connects capacitors 41 and 42 in parallel to charge capacitors 41 and 42 using switching section 47 and changeover switches 43 and 44.

On the other hand, when receiving as input by the patient from input section 29, a signal indicating start of laser puncturing or indicating start of main charging, charging control section 481 outputs a switching signal to switching section 47 to connect capacitors 41 and 42 in series.

That is, control section 48 performs preliminary charging while controlling switching section 47 to connect capacitors 41 and 42 in parallel and controls switching section 47 to connect capacitors 41 and 42 in series to make the voltage across flash lamp 26b the oscillation voltage. That is, in the present embodiment, "main charging" means capacitors 41 and 42 connecting in series. In addition, the trigger signal is outputted while capacitors 41 and 42 are connected in series to make flash lamp 26b emit light. Thus, control section 48 can raise the voltage to the oscillation voltage instantly in main charging by connecting capacitors 41 and 42 in series.

Now, operations of high-voltage generating circuit 40 configured described above will be explained.

In FIG. 18, both changeover switches 43 and 44 are switched to one terminal 43b and one terminal 44b, respectively, to connect capacitors 41 and 42 in parallel. In this state, control section 48 (specifically, charging control section 481) controls boost circuit 24 to perform preliminary charging to capacitors 41 and 42. Charging control section 481 control the charging current for capacitors 41 and 42 at this time to be 0.1 A, for example, in the same manner as embodiment 1. Then, voltage measuring circuit section measures the voltages of capacitors 41 and 42, and when the voltage across capacitors 41 and 42 becomes 200 V (the preliminary charging voltage equal to or lower than the laser oscillation level), charging control section 481 controls boost circuit section 24 to stop the supply from boost circuit section 24 to capacitors 41 and 42.

In this case, the voltage across capacitors 41 and 42 is lower than the minimum oscillation voltage (300 V), so that the laser unit section 26 does not emit laser light erroneously and safety is assured. In addition, the loss caused by the internal resistance of battery 22 is small.

Next, When information indicating start of puncturing is inputted from input section 29 to charging control section 481 by pressing the puncturing button of input section 29 by the patient, charging control section 481 switches both changeover switches 43 and 44 to the other terminal 43c and the other terminal 44c, respectively, through switching section 47 as shown in FIG. 19. That is, capacitors 41 and 42 are connected in series to form a closed circuit in which capacitors 41 and 42 and laser unit section 26 are connected in series. By this means, the voltage across capacitors 41 and 42 is added to be the voltage of 400 V (oscillation voltage), which is the main charging voltage (puncturing laser oscillation voltage enough to perform puncturing). This voltage is applied to both electrodes of flash lamp 26*b* (see FIG. 6) in laser unit section 26.

In this state, a trigger signal is outputted from charging control section 481 and is inputted to trigger circuit 26*h* through trigger signal input section 26*p* in laser unit section 26. Trigger circuit 26*h* operates by the input and flash lamp 26*b* emits light to release light energy. This light energy enters laser rod 26*c* in which Er:YAG is doped and emits laser light.

Here, after the puncturing by laser unit section 26 has been completed, or a predetermined period of time (3 seconds) has passed using a timer (see FIG. 20), charging control section 481 switches both changeover switches 43 and 44 to the one terminal 43*b* and the one terminal 44*b* again through switching section 47 to connect capacitors 41 and 42 in parallel. Therefore, even if laser unit 26 does not operate for some cause, the voltage across capacitor 41 and 42 are each 200 V, which are equal to or lower than the minimum oscillation voltage, so that safety is assured.

As described above, in the present embodiment, when a command to start puncturing is inputted from input section 29 through operation by the patient, a preliminary charging state and a main charging state in capacitors 41 and 42 can be set only by switching connection between capacitors 41 and 42. That is, laser unit section 26 is placed in the main charging state allowing laser oscillation for puncturing. Therefore, the charging duration for main charging is the switching duration of switching section 47, that is, when switching section 47 is a mechanical switch, the switching duration is about 100 ms, and when switching section 47 is an IGBT, the switching duration is equal to or shorter than 1 ms, so that additional charging to capacitors 41 and 42 is not required. Consequently, the patient substantially can perform puncturing at the same time the puncturing button in input section 29 is turned on. Moreover, additional power for that is unnecessary.

In addition, after preliminary charging, main charging to charge capacitors 41 and 42 is performed only for the switching duration of switching section 47, and current supply from battery 22 is performed during only preliminary charging. Therefore, there is no loss caused by the internal resistance of battery 22.

Here, when six hours pass (assuming that puncturing is performed after each meal) after the preliminary charging, natural discharge of about 30 V occurs and therefore the charged voltage becomes lower. Energy is required to compensate for this loss caused by natural discharge. In the present embodiment, therefore learning circuit section 284 stores the puncturing time of the patient in recording section 286 as time data using timer 282 and a time a little before the next expected puncturing time is calculated using stored data (see the table showing past statistics shown in FIG. 9). By this means, when the calculated time comes, learning circuit section 284 outputs the timing to start preliminary charging to charging control section 481 to make charging control section 481 start preliminary charging. That is, puncturing apparatus 400 starts preliminary charging before the expected puncturing time. By this means, the loss of charging voltage by natural discharge in capacitors 41 and 42 can be reduced.

Here, in puncturing apparatus 400, capacitors 41 and 42 are connected in parallel by changeover switches 43 and 44 for switching capacitors 41 and 42 in series or parallel, and therefore the state in which a high charging voltage is held in capacitors 41 and 42 for a long time can be prevented and it is possible to prevent laser unit section 26 from emitting laser light by erroneous operation.

In addition, in high-voltage generating circuit 40 in puncturing apparatus 400 according to the present embodiment, charging control section 481 charges the plurality of capacitors 41 and 42, and at the time the voltages of the plurality of capacitors and 42 each reach a predetermined threshold (e.g., the preliminary charging voltage value), the charging to capacitors 41 and 42 may be stopped.

Moreover, the switching timing at which capacitors 41 and 42 are connected in series through switching section 47 in charging control section 481 may be the timing for detecting that the pushing button and so forth, which is provided in the housing of puncturing apparatus 400, as a part of input section 29, is operated by the patient, or the timing for detecting that skin is placed in a predetermined puncturing position. Furthermore, puncturing may be performed by driving the laser unit section immediately after the switching timing for connecting in series, or the system waits for operation by the user and then puncturing may be performed by driving the laser unit section.

Furthermore, the timing for charging capacitors 41 and 42 connected in parallel may be a timing at which a cover provided to open and close the opening of the housing of puncturing apparatus 400 opens. Moreover, this timing may be a timing to perform the next puncturing estimated by learning circuit section 284 based on the time puncturing is performed in the past time.

(Embodiment 4)

Figure 21:
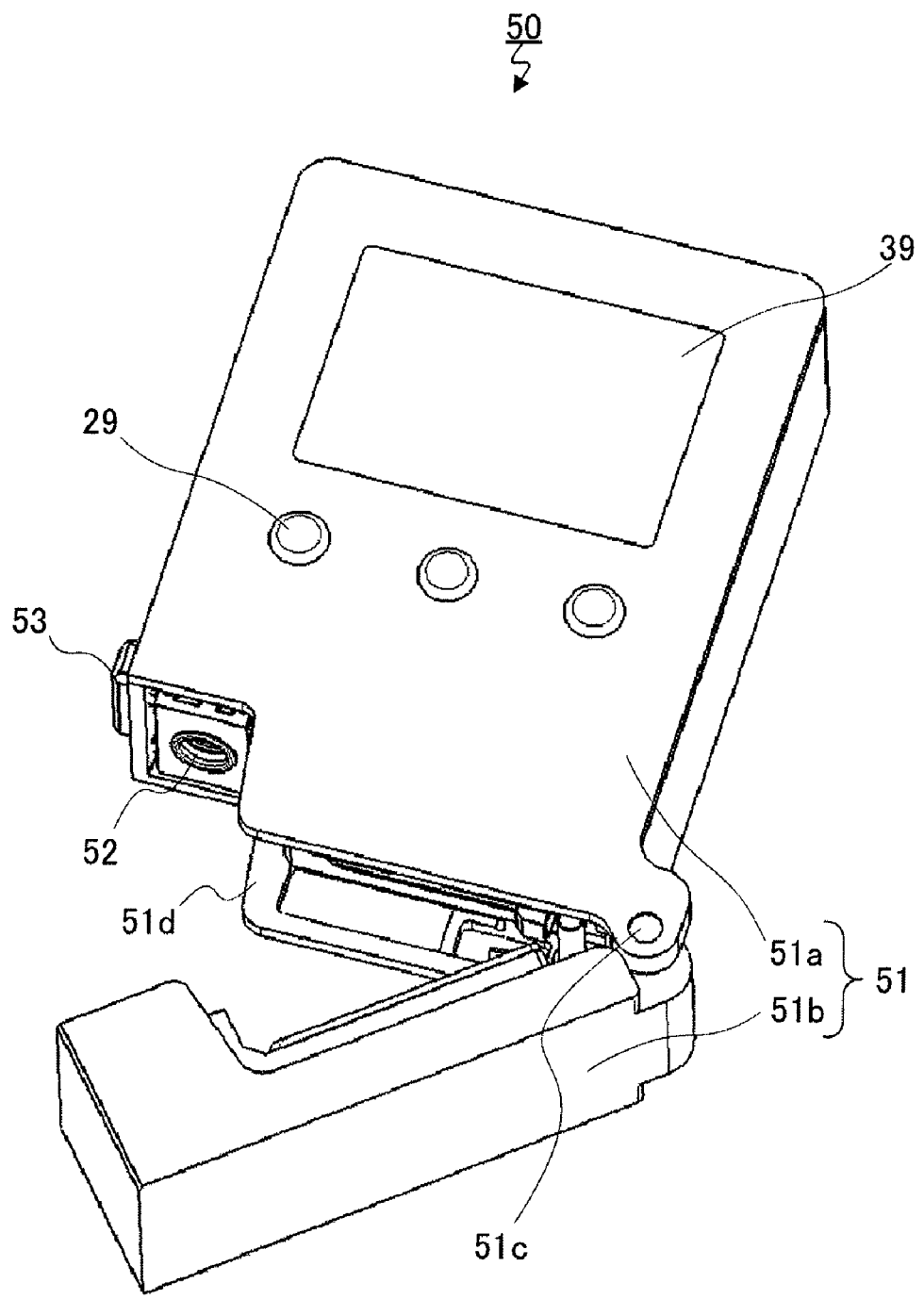
FIG. 21 is a perspective view of a puncturing apparatus according to embodiment 4.

FIG. 21 is a perspective view of puncturing apparatus 50 according to embodiment 4, and puncturing apparatus 50 is an example of puncturing apparatus 20 having high-voltage generating circuit 21, battery 22 and laser unit section 26 described in embodiment 1. Here, the same components as in embodiment 1 will be assigned the same reference numerals, and descriptions will be simplified.

Puncturing apparatus 50 shown in FIG. 21 is configured such that the patient operates puncturing apparatus 50 by holding puncturing apparatus 50 in one hand. Housing 51 of this puncturing apparatus 50 is made of resin and so forth, has an approximately rectangular solid shape and includes puncturing apparatus 20 inside. Housing 51 has housing body 51*a* that opens in its one surface side (back surface side) and cover (protective cover) 51*b* that is pivotably mounted to casing 51*a* through supporting point 51*c* and that opens and closes the opening of housing body 51*a*.

Display section 39 is located on the other surface (front surface) of housing body 51*a* and displays a state of the puncturing apparatus by input from control section 28 of high-voltage generating circuit 21 (see FIG. 3). Here, the display section is configured by LCD and so forth. In addition, input section 29 configured by a pushing button (including a puncturing button) for inputting start of puncturing of the patient is located on the other surface.

One side surface (here, bottom surface side) of housing body 51*a* is covered with cover 51*b*. In a corner of the covered opening 51*d* of housing body 51*a*, puncturing opening 52 allowing laser light from laser unit section 26 to pass through is provided in front of laser unit 26.

Puncturing opening 52 is provided to face the opening of housing body 51*a* and is exposed to outside when cover 51*b* opens.

Laser unit section 26 (not shown) of the puncturing apparatus is arranged in housing body 51*a* such that the exit hole faces puncturing opening 52 and thereby illuminates puncturing opening 52 with laser light. By this means, when covers 51b is opened to housing body 51a, puncturing opening 52 is exposed to outside, and therefore it is possible to puncture skin and so forth of the patient through puncturing opening 52.

Cover 51b stops in a state in which housing 51 is closed, that is, in a state in which the opposite end of supporting point 51 (the tip when supporting point 51c is located in the base end side) contacts housing body 51a and puncturing opening 52 is covered with cover 51b.

Being Open or closed cover 51b is detected by cover opening and closing detecting sensor 53 provided in one end (lower end) of housing body 51a, which is covered with cover 51b. Cover opening and closing detecting sensor 53 is connected to control section 28 (not shown) of high-voltage generating circuit 21 (see FIG. 3), detects the state in which the cover is open or closed and outputs the detected result to control section 28. Here, a mechanical switch is employed as cover opening and closing detecting sensor 53, cover opening and closing detecting sensor 53 is not limited to this and other configurations being capable of detecting electrical conduction may be applicable. In addition, cover opening and closing detecting sensor 53 may be an optical sensor using LED and phototransistors, and may be a magnetic sensor.

Here, in puncturing apparatus 50 according to the present embodiment, when cover opening and closing detecting sensor 53 detects cover 51b being open, control section 28 is supplied power from battery 22, makes puncturing apparatus 50 activate and outputs that fact to display section 39 to display "a power-on state" on display section 39.

In addition, when cover opening and closing detecting section 53 detects cover 51b being closed, control section 28 waits for input from cover opening and closing detecting sensor 53 and input of a preliminary charging timing and controls the puncturing apparatus to be in a power saving mode in which timer 282 (see FIG. 8) is activated. Here, the preliminary charging timing is obtained from learning circuit section 284 (see FIG. 8).

Here, in the present embodiment, control section 28 may start preliminary charging in conjunction with that cover opening and closing detecting sensor 53 detects cover 52b being open, instead of using the output from learning circuit section 284. By this means, preliminary charging can be automatically started by control section 28 only by opening cover 51b of puncturing apparatus 50 by the patient. As a result of this, the patient can perform laser puncturing only by opening cover 51b and pressing the puncturing button of input section 29.

In addition, in the present embodiment, control section 28 may start main charging in conjunction with that cover opening and closing detecting sensor 53 detects cover 52b being open. In this case, preliminary charging is finished before cover 52b opens, which is realized by starting preliminary charging immediately after the previous puncturing, and by terminating the preliminary charging before an anticipated time the patient uses the puncturing apparatus, using the output from learning circuit section 284 (see FIG. 3). By this means, the laser oscillation voltage is applied to capacitor 25 immediately only by opening cover 51b, which places the puncturing apparatus in the state allowing laser oscillation for puncturing. Therefore, when performing puncturing using puncturing apparatus 50, the patient can perform quickly laser puncturing in a short waiting period only by opening cover 51b and pressing the puncturing button.

Here, a skin detecting sensor may be provided in a portion in contact with skin around puncturing opening 52 instead of cover opening and closing detecting sensor 53 that detects cover 51b being open or closed. Control section 28 may start preliminary charging by providing this skin detecting sensor to detect contact with skin and outputting a signal indicating the contact with skin to control section 28 (specifically, charging control section 281 shown in FIG. 8). By this means, preliminary charging can be automatically started only by opening cover 51b of puncturing apparatus 50. By this means, the patient can perform laser puncturing only by opening cover 51 and pressing the puncturing button of input section 29. Moreover, in the same way, main charging may be performed based on input from the skin detecting sensor.

By this means, when the patient only places his/her skin in the puncturing position, the laser oscillation voltage is applied immediately to capacitor 25, which places the puncturing apparatus in the state allowing laser oscillation for puncturing and therefore the patient placing his/her skin in the puncturing position can perform laser puncturing immediately after pressing the puncturing button.

Input section 29 outputs, to control section 28 (specifically, charging control section 281 shown in FIG. 8), a puncturing starting signal that commands to perform main charging and emit laser light. Control section 28 calculates the time until the main charging voltage is applied to capacitor 25 based on input from each section and makes display section 39 show a countdown display.

With regard to puncturing apparatus 50 configured described above, the patient first opens cover 51b. At this time, puncturing apparatus 50 boots up from a power saving mode in conjunction with cover opening and closing sensor 53 that detects cover 51b being open and displays that fact on display section 39.

After that, the patient presses the finger-tip against puncturing opening 52. When the patient presses the pushing button of input section 29 in this state, puncturing apparatus 50 starts main charging and concurrently displays the remaining time until the puncturing is started. By this means, the patient can confirm the timing the patient is punctured by sight.

After the countdown display on display section is finished, laser light is emitted from laser unit section 26 (see FIG. 3) and illuminates the skin of the patient through puncturing opening 52. By this means, the skin is punctured by ablation, so that blood exudes. Thus, blood exuding from skin by puncturing is used in a blood test apparatus and so forth, so that the blood sugar level and so forth are measured.

After puncturing apparatus 50 is used, cover 51b is closed and the puncturing operation is finished. By closing cover 51b, puncturing apparatus 50 operates in a power saving mode and prepares for the next preliminary charging. Thus, puncturing apparatus 50 operates in the power saving mode without power-off even if puncturing apparatus 50 is not being used. Then, when control section 28 detects the timing to start preliminary charging, puncturing apparatus 50 automatically starts preliminary charging.

Here, in the present embodiment, preliminary charging may be started at the time the previous puncturing is finished. By this means, the patient can perform puncturing immediately after (after 2.7 seconds) the main charging starting operation. Here, the timing to start preliminary charging is outputted from learning circuit section 284 shown in FIG. 8, and therefore the loss of the charged voltage caused by natural discharge of about 30 V when, for example, 6 hours pass after preliminary charging (assuming that puncturing is performed after each meal). That is, as described above, learning circuit section 284 is configured to store the puncturing time of the patient in recording section 286 as time data using timer 282 and so forth, calculates the next anticipated puncturing time based on this stored past statistics and outputs the time a little before the calculated next anticipated puncturing time to charging control section 281 as the timing to start preliminary charging. By this means, in puncturing apparatus 50, when the next puncturing time approaches, preliminary charging is automatically started and the loss of the charged voltage applied to capacitor 25 while puncturing is not performed can be reduced. Here, in puncturing apparatus 50 according to the present embodiment, high-voltage generating circuit 31 according to embodiment 2 or high-voltage generating circuit 40 according to embodiment 3 may be employed instead of high-voltage generating circuit 21.

(Embodiment 5)

Figure 22:
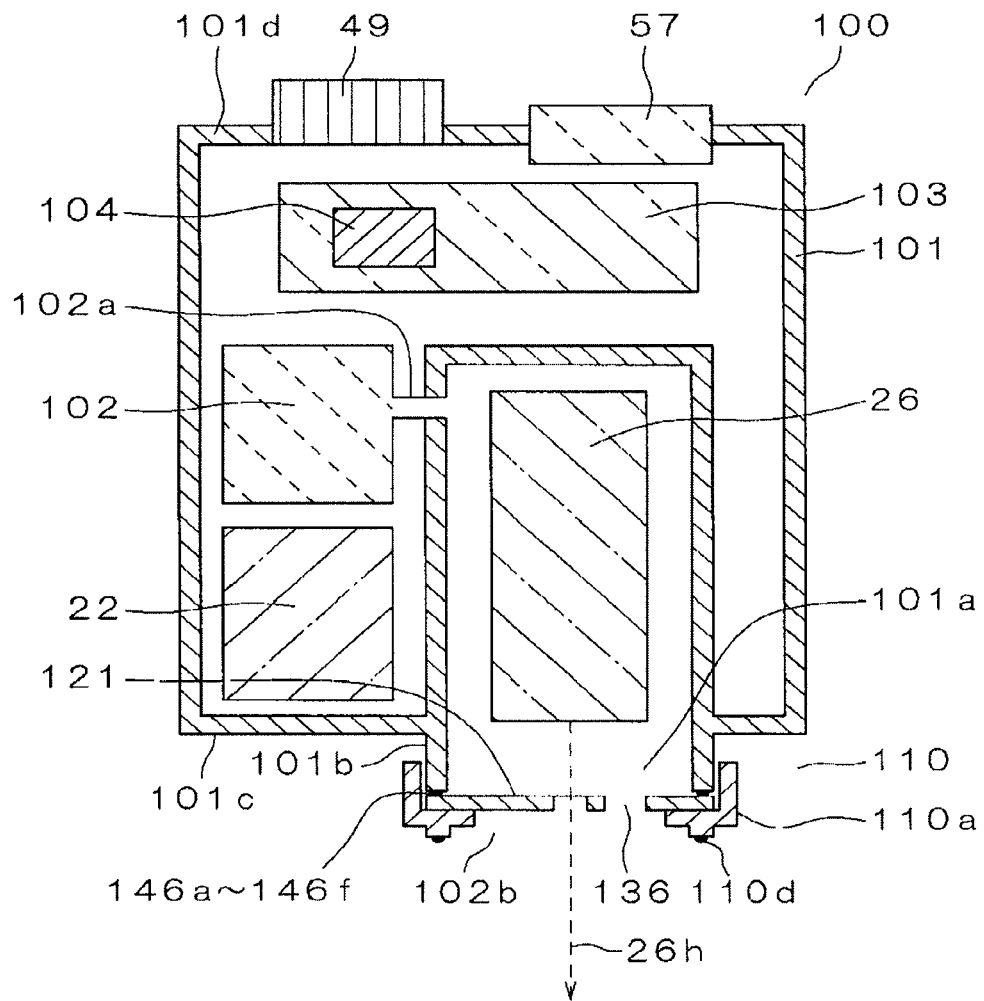
FIG. 22 is a cross sectional view of a blood test apparatus according to embodiment 5.

FIG. 22 is a block diagram of blood test apparatus 200 according to embodiment 5 of the present invention. Here, the same components as in embodiments 1 to 3 will be assigned the same reference numerals and descriptions will be omitted. Here, blood test apparatus 100 according to the present embodiment has an electrical circuit section 103 including high-voltage generating circuit 21a (see FIG. 26) having the same configuration as high-voltage generating circuit 21 according to embodiment 1, except for display section 39 and input section 29, and also has battery 22 and laser unit section 26. Here, display section 39 and input section 29 of high-voltage generating circuit 21 are equivalent to display section 57 and input section 49 provided in housing 101 of blood test apparatus 100, respectively.

Housing 101 of blood test apparatus 100 shown in FIG. 22 is made of resin, and cylindrical-shaped cylindrical body 101b having puncturing section 101a is provided in housing 101c, which is one-half of housing 101. Laser unit section 26 is mounted inside this cylindrical body 101b to face puncturing section 101a. In addition, negative pressure means 102 is mounted to this cylindrical body 101b coupled through negative pressure path 102a. Laser puncturing section 26 and electrical circuit section 102 connected to negative pressure means 102 are mounted between cylindrical body 101b and housing 101d, which is the other half of housing 101. High-voltage generating circuit 21a equivalent to high-voltage generating circuit 21 and measuring circuit section 104 are provided in this electrical circuit section 103. Moreover, battery 22 is replaceably housed adjacent to cylindrical body 101b.

Input section 49 and display section 57 are provided in housing 101d, which is the other half of housing 101. Power supply switch 49a (see FIG. 26), preliminary charging button 49b (see FIG. 26), main charging button 49c (see FIG. 26), puncturing button 49d (see FIG. 26) and laser power adjusting knob 49e (see FIG. 26) are provided in input section 49. Here, preliminary charging button 49b and main charging button 49c correspond to input section 29 in high-voltage generating circuit 21 according to embodiment 1.

Sensor unit 110 is removably mounted between the tip of cylindrical body 101b and puncturing section 101a. This sensor unit 110 is composed of holder 110a and blood sensor (hereinafter referred to as a sensor) 121, and sensor 121 is removably mounted in holder 110a.

Connection electrodes 131a to 135a and 133c (see FIG. 25A) provided in sensor 121 are connected to electrical circuit section 103 through connectors 146a to 146f provided on the tip of cylindrical body 101b.

Negative pressure means 102 sucks in blood from skin with a negative pressure. Here, in the present embodiment, although high-voltage generating circuit 21a is applied to blood test apparatus 100 having negative pressure means 102, high-voltage generating circuit 21a is applicable to a blood test apparatus without negative pressure means 102 (e.g., only by kneading skin). A negative pressure created by this negative pressure means 102 is introduced into negative pressure chamber 102b through negative pressure path 102a and through-hole 135 (see FIG. 24 and FIG. 25A) formed in sensor 121.

Figure 23:
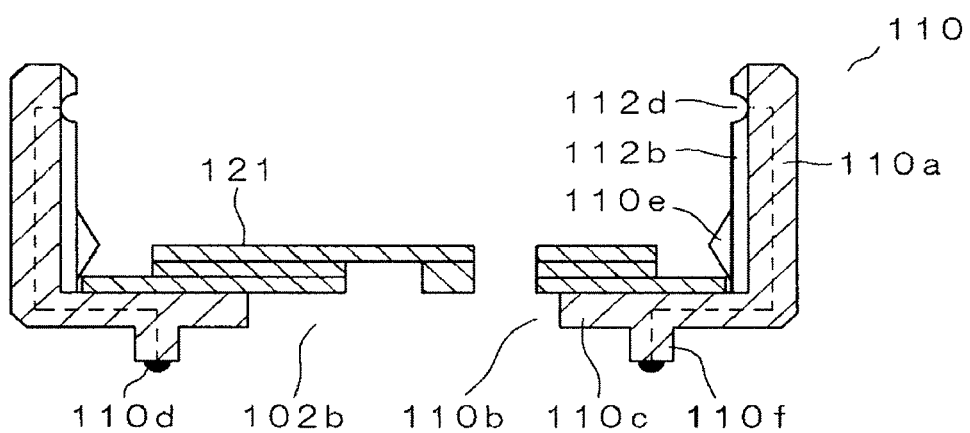
FIG. 23 is a cross sectional view of a sensor unit.

FIG. 23 is a cross sectional view of sensor unit 110. Pedestal 110c is provided in holder 110a and has hole 110 at its center, and sensor 121 is placed on this pedestal 110c. Then, this sensor 121 is locked by locking convex part 110e formed in holder 110a. In addition, ring-shaped convex part 110f projecting downward is formed below pedestal 110c and constitutes negative pressure chamber 102b.

Skin detecting sensor 110d that detects contact with skin is provided on convex part 110f. A signal from this skin detecting sensor 110d is connected to a terminal exposing in concave part 112d formed in guide 112b via a conducting line.

Skin detecting sensor 110d detects the contact resistance of skin 9 and is configured by a conductive electrode. Then, signals from skin detecting sensor 110d are connected such that the plurality of concave parts 112d are divide into two 180 degrees apart from each other. The purpose for this is to capture signals from convex part 112c fitting in these concave part 112d from positions 180 degrees apart from each other, and therefore it is possible to capture signals regardless of the direction (angle) to insert sensor unit 110. Here, the relationship between concave part 112d formed in sensor unit 110 and convex part 112c formed outside cylindrical body 101b may be reversed.

Figure 24:
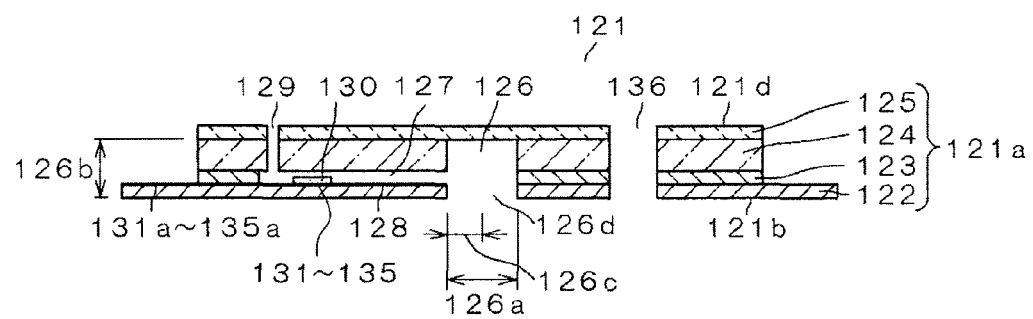
FIG. 24 is a cross sectional view of a sensor.

FIG. 24 is a cross sectional view of sensor 121. Base body 121a constituting this sensor 121 is composed of substrate 122, first spacer 123 pasted on the upper surface of this substrate 122, cover 124 pasted on the upper surface of this spacer 123 and film 125 pasted on the upper surface of this cover 124, has an approximately circular shape and is formed of a plate.

Storing section 126, which contacts skin and samples blood from the skin in contact, is formed in approximately the center of base body 121a. Storing section 126 opens toward bottom surface 121b of base body 121a and the top surface 121d side is sealed with film 125. Storing section 126 has a cylindrical shape and height 126b from the opening surface, which forms opening 126d, is larger than radius (½ of diameter 126a) 126c of a cylindrical shape. Therefore, sufficiently large blood droplet can be obtained.

One end of supply path 127 of blood is coupled with this storing section 126, and supply path 127 is a path for introducing blood stored in storing section 126 into detecting section 128 formed above supply path 127 by capillary action. In addition, the other end of this supply path 127 is coupled to air hole 129. Here, a hydrophilic material is used in supply path 127.

Reagent 130 is placed on detecting section 128. Reagent 130 can be obtained by adding and dissolving PQQ-GDH (0.1 to 5.0 U/sensor), potassium ferricyanide (10 to 200 millimoles), maltitol (1 to 50 millimoles) and taurine (20 to 200 millimoles) in a CMC solution of 0.01 to 2.0 wt % to prepare a reagent solution, by dropping the reagent solution on detection electrodes 131 and 133 (see FIG. 25A) forming detecting section 128 formed on substrate 122 and drying.

Through-hole 136, which is a negative pressure path in sensor 121, is formed between storing section 126 and base body 121a. Here, this through-hole 136 has a diameter of 1.500 mm. The negative pressure path formed by this through-hole 136 may be coupled with storing section 126 from the film 125 side by providing a slit in cover 124.

Figure 25A:
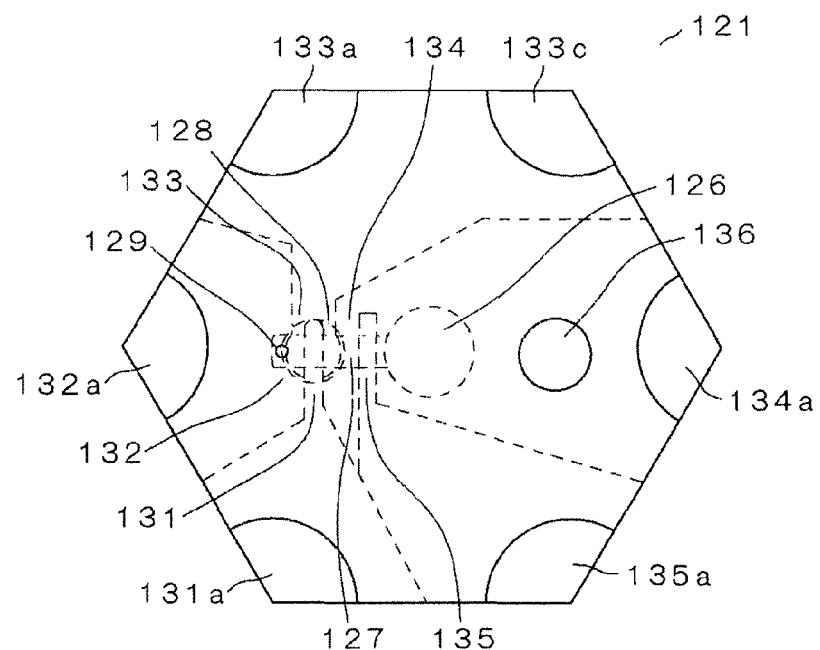
FIG. 25A is a transparent plane view of the sensor.
Figure 25B:
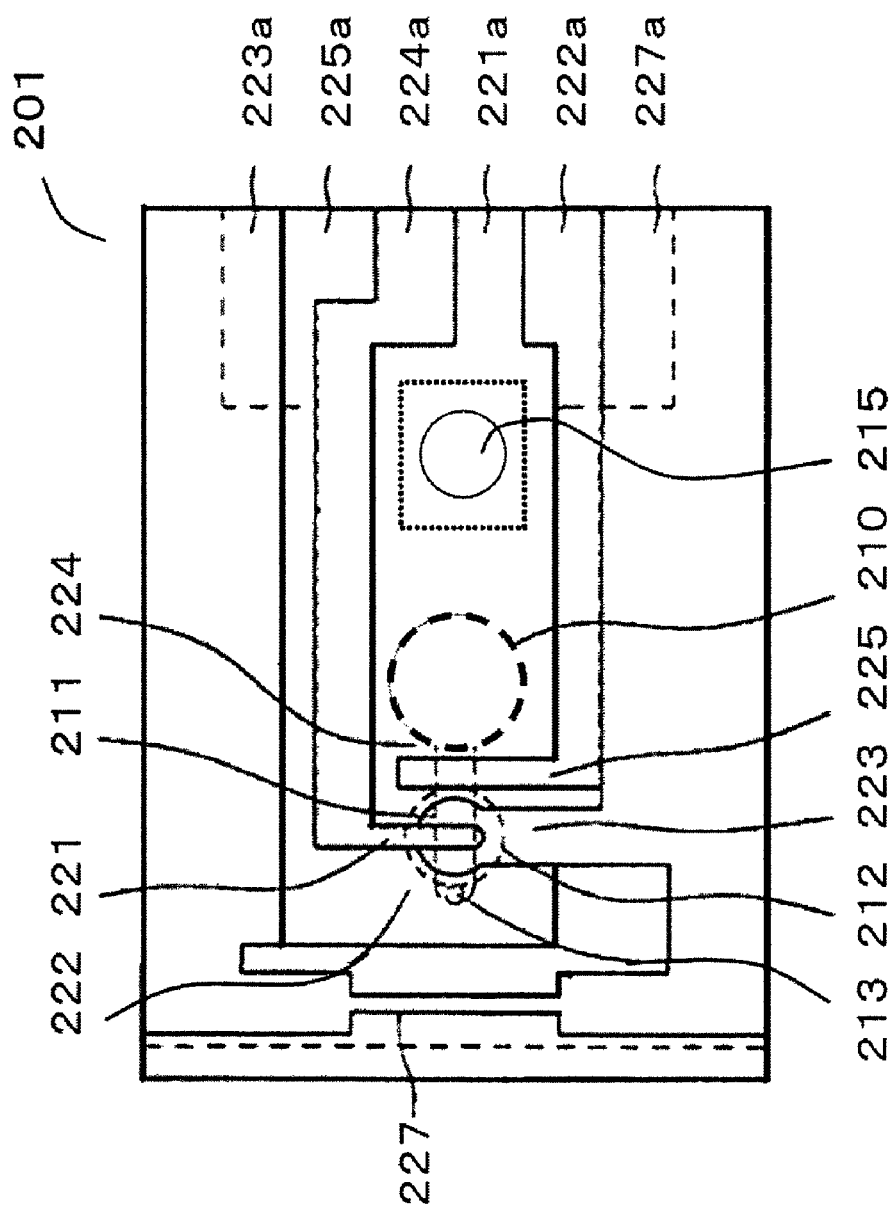
FIG. 25B is a transparent plane view of the sensor.

FIG. 25A and FIG. 25B are transparent plane views of sensors, respectively. Here, sensor 121 shown in FIG. 25A has a regular hexagonal shape and sensor 201 shown in FIG. 25B has a quadrangular shape. Although sensors 121 and 201 have different shapes one another, the cross-sectional structures are the same as shown in FIG. 24. Therefore, sensors 121 and 201 have the same function.

FIG. 25A is a transparent plane view of sensor 121. Sensor 121 has a regular hexagonal shape, and in each of six top parts of the regular hexagon, connection electrodes 131a to 135a and reference electrode 133c connected to connectors 146 (146a to 146f), which are provided in the tip of cylindrical body 101b provided in blood test apparatus 100, are formed.

Storing section 126 is provided in approximately the center of sensor 121 having a regular hexagonal shape. In addition, supply path 127 connected to storing section 126 at its one end is provided toward detection electrode 132. Then, the other end of this supply path 127 is coupled to air hole 129. Storing section 126, detection electrode 134 connected to connection electrode 134a, detection electrode 135 connected to connection electrode 135a, again detection electrode 134 connected to connection electrode 134a, detection electrode 133 connected to connection electrode 133a and reference electrode 133c, detection electrode 131 connected to connection electrode 131a, again detection electrode 133 connected to connection electrode 133a and reference electrode 133c and detection electrode 132 connected to connection electrode 132a, are provided on supply path 127, in the order described. In addition, reagent 130 (see FIG. 24) is placed on detection electrodes 131 and 133. Through-hole 136 is provided between storing section 126 and connection electrode 134a.

With sensor 121 according to the present embodiment, since film 125 allowing laser light to pass through has already been attached, lens 26c mounted in laser puncturing apparatus 26 is not stained with scattered materials at the time to perform puncturing. In addition, film is replaced at the same time as sensor 121 is replaced. Therefore, film 125 is replaced in the same time as sensor 121 is replaced without thinking of replacement of film 125, so that the burden of replacement is removed and film 125 can be easily replaced.

Moreover, since height 126b from the surface of opening 126d to film 125 is larger than radius 126c of the cylindrical shape, sufficiently sized blood droplet 10a can be produced in storing section 126. Furthermore, it is not necessary to provide film as a separate component for this sensor 121 and therefore the overall cost can be reduced. Furthermore, sensor unit 110 is configured by mounting this sensor 121 in holder 110a, and thereby the thickness of sensor 121 does not appear at all.

Next, sensor 201 having a quadrangular shape, which is another example in the present embodiment, will be described with reference to FIG. 25B.

Sensor 201 shown in FIG. 25B has a structure with six electrodes (221a, 222a, 223a, 224a 225a and 227a), including identification electrode 227a. The cross-sectional shape of this sensor 201 is the same as that of hexagonal sensor 121 described above as shown in FIG. 24, and sensor 201 has a four-layer structure including a film.

Storing section 210 is formed in approximately the center of sensor 201, and connection electrodes 221a to 225a (equivalent to connection electrodes 131a to 135a shown in FIG. 25A) and identification electrode 227a (equivalent to reference electrode 133c shown in FIG. 25A) are formed in one end of sensor 201. Through-hole 215 (equivalent to through-hole 136 shown in FIG. 25A) is formed between those connection electrodes 221a to 225a and identification electrode 227, and storing section 210. Here, blood taken in storing section 210 is taken in detecting section 212 at a breath (a fixed flow rate) by capillary action through supply path 211. Then, the blood sugar level of blood is measured.

Here, detecting section 212 has the same function as that of detecting section 128 shown in FIG. 25A.

Storing section 210, detection electrode 224, detection electrode 225, again detection electrode 224, detection electrode 23, detection electrode 221, again detection electrode 223 and detection electrode 222 are provided on supply path 211 (equivalent to supply path 127 in sensor 121 shown in FIG. 25A), in the order described. In addition, reagent 130 (see FIG. 24) is placed on detection electrode 221 and 223. Identifying section 227 formed by a conductor pattern is formed between detection electrode 223 and identification electrode 227a. Here, the other end of supply path 211 is coupled to air hole 213 and therefore the same effect as the configuration in which supply path 127 is coupled to air hole 129, shown in FIG. 25A is achieved.

Blood test apparatus 100 (see FIG. 22) can detect whether or not sensor 201 is mounted in holder 110a and then mounted in cylindrical body 101b by detecting whether or not there is electrical conduction between connection electrode 223a and identification electrode 227a.

In addition, it is possible to store information of the calibration curve to be used and also manufacturing information by changing the electrical resistance of identifying section 227. Therefore, a blood test can be more accurately performed by using those information. Here, although an example having identification electrode 227a is shown in FIG. 25B, identification electrode 227a may be omitted.

Although sensor 201 in FIG. 25B is formed by a rectangular plate-like body, the shape of sensor 201 is not limited in the present invention. The shape of sensor 201 may be a square, or a polygon other than a square, or a semicircle.

Figure 26:
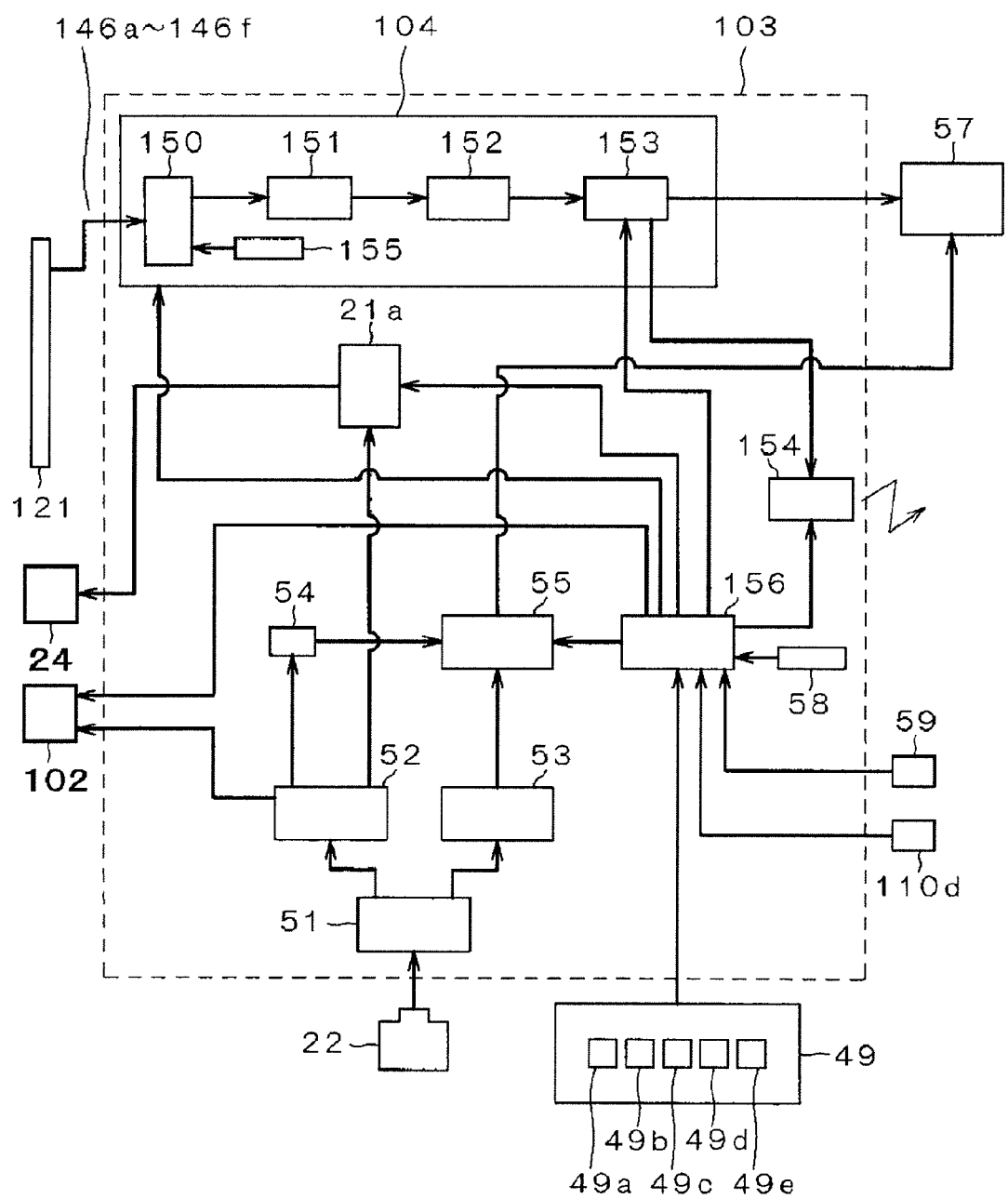
FIG. 26 is a block diagram of an electrical circuit section and its neighborhood in the blood test apparatus according to embodiment 5 of the present invention.

FIG. 26 is a block diagram of electrical circuit section 103 and its neighborhood in the blood test apparatus according to embodiment 5 of the present invention. Electrical circuit section 103 according to the present embodiment principally has a configuration including blood measuring circuit section 104 in addition to high-voltage generating circuit 21a equivalent to high-voltage generating circuit 21. Therefore, the same components will be assigned same reference numerals and additional matters will be mainly described.

Electrical circuit section 103 has voltage and current detecting section 51 that detects the current and the voltage of battery 22; power consumption measuring section 52 that measure power consumption of the entire system; remaining battery level measuring section 53 that measures the remaining level of the battery; memory 54; remaining puncturing calculation section 55; timer 58; communicating section 154; and control section 156, in addition to high-voltage generating circuit 21a and measurement circuit section 104. Operation information is inputted to control section 156 of electrical circuit section 103, from input section 49, such as power supply switch 49a, preliminary charging button 49b (equivalent to input section 29 shown in FIG. 3), main charging button 49c (equivalent to input section 29 shown in FIG. 3), puncturing button 49d, laser power adjusting knob 49e and so forth. In addition, control section 156 makes display section 57 configured by LCD output the number of remaining puncturing operations calculated by remaining puncturing calculation section 55. Here, a high-voltage generating circuit equivalent to a part of high voltage generating circuit 31 or 40 not including display section 39 and input section 29 may be employed instead of high-voltage generating circuit 21a. In this case, display section 39 and input section 29 in high-voltage generating circuit 31 or 40 have the same configuration as those of input section 49 and display section 57 provided in housing 101 of blood test apparatus 100.

In FIG. 26, signals from connection electrodes 131a to 135a in sensor 121 (equivalent to connection electrodes 221a to 225a in sensor 201) and reference electrode 133c (equivalent to identification electrode 227a in sensor 201) are inputted to switching circuit 150 of measuring circuit section 104 through connectors 146a to 146f. The output of switching circuit 150, which is inputted from connection electrodes 131a to 135a and reference electrode 133c, is connected to the input of current/voltage converter 151. Then, the output is connected to the output of computing section 153 through analog/digital convertor (hereinafter referred to as "A/D convertor"). The output of this computing section is connected to display section 57 made of liquid crystal and transmitting section 154. In addition, reference voltage source 155 is connected to switching circuit 150. Here, this reference voltage source 155 may be a ground potential.

Control section 156 is configured by a microcomputer and so forth, controls entirely high-voltage generating circuit 21a and blood test apparatus 100, including puncturing operation and blood test operation, and performs processing by remaining puncturing calculation section 55, including calculating the number of remaining puncturing operations and displaying the number of remaining puncturing operations. Signals from input section 49, timer 58, cover opening and closing detecting sensor 59 and skin detecting sensor 110d (see FIG. 23) are inputted to control section 156. Control section 156 outputs each control signal to the control terminal of switching circuit 150, computing section 153, high-voltage generating circuit 21a, negative pressure means 102, remaining puncturing calculation section 55 and communicating section 154.

Voltage and current detecting section 51 detects the voltage of battery 22 and the current flowing from battery 22 and outputs the voltage and current detecting result to power consumption measuring section 52 and remaining battery level measuring section 53.

Power consumption measuring section 52 calculates the power consumption by adding the value of current (A) flowing out from the battery 22 by one test operation (i.e., a series of operations including supplying a negative pressure, puncturing and measuring), voltage (V) of battery 22 and period (h) required for the test. Blood test operation means operations associated with the test, that is a series of operations including supplying a negative pressure, puncturing, measuring and displaying the result.

Power consumption measuring section 52 is a power consumption measuring section that measures the power consumption of the entire blood component measuring system and is composed of laser power consumption measuring section, negative pressure power consumption measuring section and blood test circuit power consumption measuring section. Here, the laser power consumption measuring section measures the power consumption of laser emitting device 26 by one test (puncturing) operation. The negative pressure power consumption measuring section measures the power consumption of negative pressure means 102 for one test (puncturing and measuring) operation. The blood test measuring circuit power consumption measuring section measures the power consumption of measuring circuit section 104 for one test (measuring) operation.

Here, power consumption measuring section 52 may measure the power consumption for a series of operations in a blood test or may calculate the sum of the power consumption for each of unit section 26, negative pressure means 102 and measuring circuit section 104.

Remaining battery level measuring section 53 is configured by a remaining level measurement-dedicated IC and measures the remaining battery level of battery 22. Remaining battery level measuring section 53 adds the voltage value or the current value in the time of non-loading and subtracts the added result from the capacity at the time battery 22 is replaced to calculate the remaining battery level.

Memory 54 is configured by a nonvolatile memory and so forth, such as an EEPROM, a flash memory and so forth and stores data of each power consumption measured in power consumption measuring section 52 every puncturing. With the present embodiment, memory 54 stores data of past power consumption for learning the number of times of blood tests depending on the state in which the user uses the puncturing apparatus. Memory 54 stores data of each measurement measured by power consumption measuring section 52 and the stored data is read by remaining puncturing calculation section 55.

Remaining puncturing calculation section 55 calculates the number of remaining puncturing operations by dividing the measured remaining battery level by the power consumption for one puncturing.

The power consumed in laser emitting device 26 and negative pressure means 102 is predominant, so that the power consumption of display section 57 and electrical circuit section 103, which is the power consumed by the system, may be disregard. However, in order to improve the accuracy of computation, the power consumption preferably includes the power consumption of the system as well as the power consumption of laser emitting device 26 and negative pressure means 102. In addition, another embodiment may be applicable where remaining puncturing calculation section 55 calculates the number of remaining puncturing operations based on the average of the past power consumption stored in memory 54. The average of past power consumption stored in memory 54 is used, so that the accuracy of computation can be improved.

Measuring circuit section 104 is a blood component measuring section that measures and test blood components and is composed of reference voltage source 155, switching circuit 150, current/voltage convertor 151, A/D convertor 152 and computing section 153. The output of switching section 150 is connected to an input of current/voltage convertor 151 and the output of current/voltage convertor 151 is connected to the output of computing section 153 through A/D convertor 152. The output of computing section 153 is communication section 154 and display section 260. Moreover, reference voltage source 155 is connected to switching circuit 150. Reference voltage source 155 may be a ground potential.

Timer 58 measures the time required to swell skin. The time for high-voltage charging and the time for swelling skin may be measured as different time one another.

Display section 57 is composed of LCD, a display driver circuit and so forth and displays puncturing information including the number of remaining puncturing operations. Display section 57 has a function as a broadcast means to issue a warning when the number of times of blood tests is equal to or less than a predetermined number of times. For example, display section 57 displays in red for highlighting a warning when the number of times of blood tests is equal to or less than a predetermined number of times. In addition, display section 57 displays an effect (warning mark, blinking and so forth) for highlighting a warning at the time for displaying.

Now, operations of blood test apparatus 100 configured as described above will be explained.

First, measuring operation of electrical circuit section 103 will be explained.

First, switching circuit 150 is switched, and a detection electrode serving as a working electrode for measuring blood components is connected to current and voltage convertor 151 through the determined connector. In addition, a detection electrode serving as a detecting electrode for detecting inflow of blood is connected to reference voltage source 155 though the determined connector.

Then, a constant voltage is applied between the detection electrode serving as a working electrode and the detection electrode serving as a detecting electrode. In this state, a current flows between two detection electrodes when blood flows in the detecting section. This current is converted into a voltage by current/voltage convertor 151, and the voltage value is converted into a digital value by A/D convertor 152. Then, this digital value is outputted to computing section 153. Computing section 153 detects that blood has sufficiently flown in based on the digital value.

When the detecting section does not detect blood even if a predetermined period of time has passed and when the amount of blood is not appropriate, the control section may make a warning means work to give an alarm and make display section 57 display the content of measures.

Next, glucose, which is a component of blood, will be measured. To measure the glucose level, first, switching circuit 150 is switched by a command from control section 156, and the detection electrode serving as a working electrode for measuring the glucose level is connected to current/voltage convertor 151 through the connector. In addition, the detection electrode serving as a counter electrode for measuring the glucose level is connected to reference voltage source 155 through the connector.

For example, while the glucose in blood and its oxidation-reduction enzyme react for a given period of time, current/voltage convertor 151 and reference voltage source 155 are turned off. Then, after a certain period of time (1 to 10 seconds) has passed, a certain voltage (0.2 to 0.5 V) is applied between the detection electrode serving as a working electrode and the detection electrode serving as a counter electrode by a command from control section 156. Then, the current flown between two detection electrodes is converted into a voltage by current/voltage convertor 151. This voltage value is converted into a digital value by A/D convertor 152. This digital value is outputted to computing section 153. Computing section 153 calculates the glucose level based on this digital value.

After the glucose level is measured, the Hct (hematocrit) value will be measured. First, switching circuit 150 is switched by a command from control section 156. Then, the detection electrode serving as a working electrode for measuring the Hct value is connected to current/voltage convertor 156 through the connector. In addition, the detection electrode serving as a counter electrode for measuring the Hct value is connected to reference voltage source 155.

Next, a certain voltage (2 V to 3 V) is applied between the detection electrode serving as a working electrode and the detection electrode serving as a counter electrode, by a command from control section 156. The current flowing between two detection electrodes is converted into a voltage by current/voltage convertor 151. This voltage value is converted into a digital value by A/D convertor 152. This digital value is outputted to computing section 153. Computing section 153 calculates the Hct value based on this digital value.

With reference to a calibration curve or calibration curve table determined in advance, the glucose level is corrected using the calculated Hct value. The correction result is displayed on display section 57.

In addition, the correction result may be transmitted from communicating section 82 to an injection device for injecting insulin. Although a radio wave may be used for this transmission, transmission is preferably performed by optical communication that does not interfere with medical equipment. When the dose of insulin to administer is automatically set based on the measurement data transmitted to the injection device, it is not necessary to set the dose of insulin to be administered by the patient, which removes the burden with setting. Moreover, since the dose of insulin can be set in the injection device without human work, setting error can be prevented.

Figure 27:
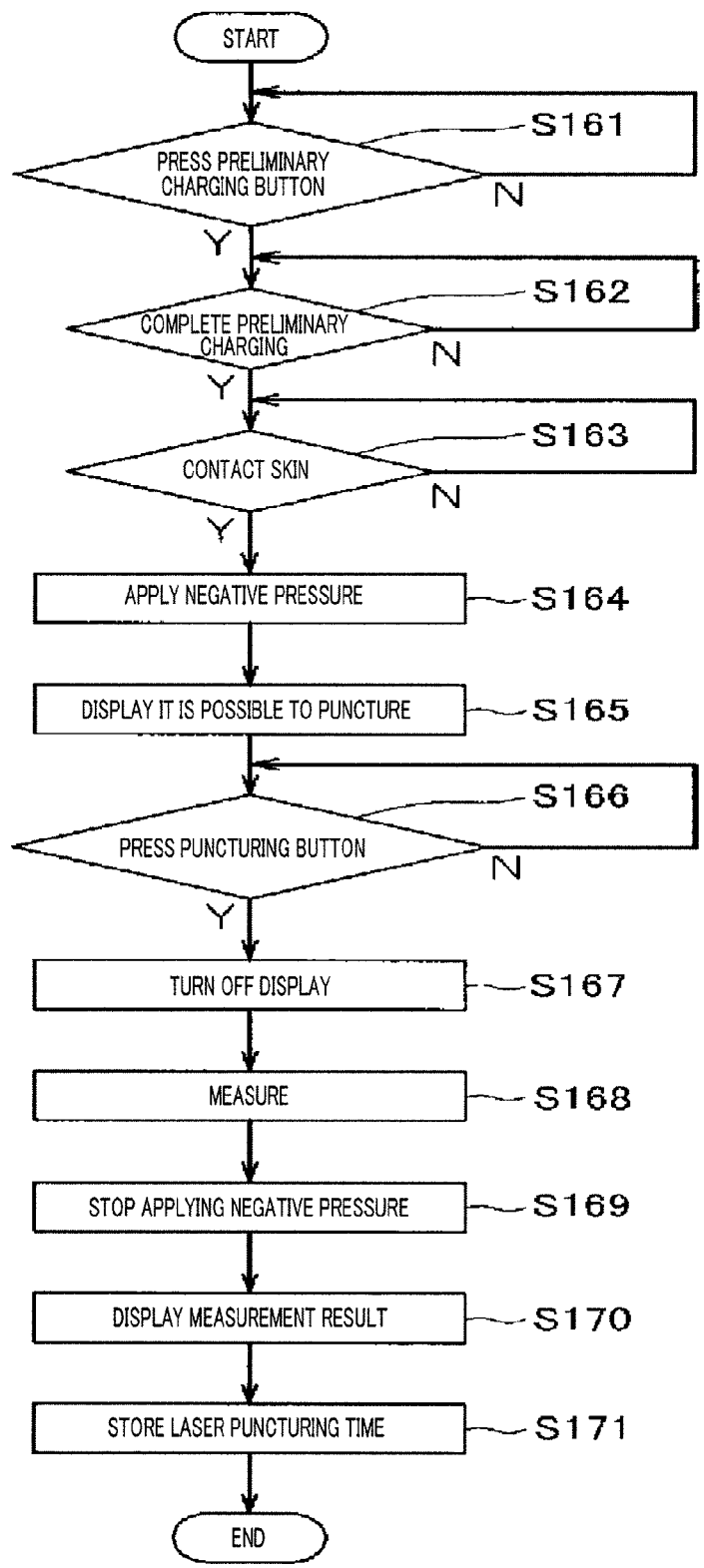
FIG. 27 is a flow chart explaining a test method of the blood test apparatus.

Next, a test method of blood test apparatus 100 will be described with reference to FIG. 27. First, in step S161, preliminary charging button 49b waits to be pressed. When this preliminary charging button 49b is turned on, the step moves to step S162 and completion of preliminary charging is waited. Here, the preliminary charging is performed by high-voltage generating circuit 21a.

When the preliminary charging is completed, an indication to complete the preliminary charging and to promote to contact puncturing section 101a with skin 9 is displayed on display section 57. The patient touches puncturing section 101 of blood test apparatus 100 with skin 9 of his/her patient following this indication. This contact with skin 9 is detected based on the output of skin detecting sensor 110d. When the contact with skin 9 is checked, the step moves to step S164 and negative pressure means 102 is operated to apply a negative pressure to inside negative pressure chamber 102 provided in puncturing section 101a. Skin 9 swells by applying a negative pressure.

When the current is changed as a result of the operation of negative pressure means 102 or when timer 58 measures the passage of a predetermined period of time, it is determined that skin 9 has swelled enough to be punctured, and the step moves to step 165. In step S165, an indication that it is possible to perform puncturing is displayed on display section 57 on the condition that there is the output from skin detecting sensor 110d (AND condition). Then, the step moves to step S166 and puncturing button 49d waits to be pressed. When this puncturing button 49d is pressed, the pressing signal of this puncturing button 49d is inputted to high-voltage generating circuit 21a and the step moves to step S167. Here, the condition that there is output from skin detecting sensor 110d applies again. The reason for this is to prevent laser light from emitting erroneously despite that puncturing section 101a of blood test apparatus 100 is not in contact with skin 9.

In step S167, the display performed in step S165 is turned off. Then, the step moves to step S168. In step S168, blood exuding by puncturing skin 9 is taken in storing section 126 of sensor 121. Blood taken in this storing section 126 is taken in detecting section 128 at a breath (a fixed flow rate) by capillary action through supply path 127. Then, the blood sugar level of blood is measured.

When the blood sugar level is measured in step S168, the step moves to step S162 and negative pressure means 102 is turned off. Then, the step moves to step S170. In step S170, the measured blood sugar level is displayed on display section 57. Here, negative pressure means 102 may be turned off at the time blood reaches detection electrode 142.

After the measurement result is displayed in step S170, the step moves to step S171, the puncturing date and the puncturing time are stored in memory 54. Purposes for this are to manage the puncturing time, to perform statistical processing of this puncturing time and to notify the patient to perform preliminary charging and prevent forgetting puncturing when the puncturing time approaches.

Here, with the present embodiment, preliminary charging is started at the time the previous puncturing is completed, and therefore the user can perform puncturing immediately after (after 2.7 seconds) the charging starting operation. Here, when six hours (assuming that puncturing is performed after each meal) pass after preliminary charging, the charging voltage reduces by about 30 V due to natural discharge. Energy is required to compensate for the loss caused by this natural discharge. In order to reduce this loss, for example a learning function may be provided. That is, the time at which the patient performs puncturing is stored as time data using a timer and so forth, and preliminary charging is automatically started a little before the next expected puncturing time (calculated by past statistics) based on the time data. By this means, the loss can be reduced by an effect of preliminary charging.

In addition, although blood test apparatus 100 according to the present embodiment has a configuration in which preliminary charging is started by pressing preliminary charging button 49b, start of preliminary charging is not limited this and preliminary charging may be started using cover opening and closing detecting sensor 59 or skin detecting sensor 110d (see FIG. 23).

For example, when cover opening and closing detecting sensor 59 detects cover 52b being open, or when skin detecting sensor 110d detects contact with skin, preliminary charging is started in high-voltage generating circuit 21a through control section 156 at the timing at which the detection result is inputted. By this means, the preliminary charging in high-voltage generating section 21a can be automatically started only by which the patient opens cover 51b of puncturing section 50 or places the finger in a puncturing position. As a result of this, the patient can perform laser puncturing only by opening cover 51b, placing the finger in a puncturing position or pressing the puncturing button of input section 29.

In addition, when cover opening and closing detecting sensor 59 (see FIG. 23) detects the cover being open, control section 28 may start main charging in conjunction with the detection. In this case, although the preliminary charging has been finished before the cover is opened or before the finger is placed in the puncturing position, the above-described main charging timing can be realized by starting preliminary charging immediately after the previous puncturing or by finishing preliminary charging before the anticipated time the puncturing apparatus is used, using the output from learning circuit section 284 (see FIG. 3).

Therefore, the laser oscillation voltage is applied to capacitor 25 immediately only by opening the cover or placing the finger in a puncturing position, and therefore it is possible to place the puncturing apparatus in the state allowing laser oscillation for puncturing. By this means, the patient can perform quickly laser puncturing without waiting, by opening the cover or placing the finger in a puncturing position.

Here, although blood test apparatus 100 of the present embodiment has been described using high-voltage generating circuit 21 according to embodiment 1, it goes without saying that high-voltage generating circuit 21a, 31 and 40 may be applicable instead of high-voltage generating circuit 21.

The disclosures of Japanese Patent Application No. 2007-265175, filed on Oct. 11, 2007 and Japanese Patent Application No. 2007-265176, filed on Oct. 11, 2007, including the specifications, drawings and abstracts, are incorporated herein by reference in their entirety.

Industrial Applicability

The high-voltage generating circuit according to the present invention provides an effect of allowing the voltage for laser puncturing to rise to the laser oscillation level with a small power loss and in a short time and is useful to a puncturing apparatus, blood test apparatus and so forth using a laser puncturing device.

The invention claimed is:

1. A high-voltage generating circuit that drives a laser puncturing unit that oscillates laser light and punctures skin, the high-voltage generating circuit comprising:
    a capacitor that is charged with an electric charge and supplies power to the laser puncturing unit;
    a boost circuit that supplies a current to the capacitor;
    a voltage measurer that measures a voltage of the capacitor; and
    a controller that controls the boost circuit based on a command from a user or the voltage of the capacitor,
    wherein the controller controls the boost circuit to output a current of a first value into the capacitor to start a first stage charging operation at a first timing, and controls the boost circuit to output a current of a second value, higher than the first value, into the capacitor to start a second stage charging operation at a second timing, later than the first timing, and
    the capacitor is charged from a discharged-state to an amount of charge that is sufficient to drive the laser puncturing unit, through the first stage charging operation and the second stage charging operation.

2. The high-voltage generating circuit according to claim 1, wherein the controller stops charging the capacitor with the current of the first value at the second timing.

3. The high-voltage generating circuit according to claim 1, wherein after starting charging the capacitor with the current of the first value, the controller stops supplying the current to the capacitor when the voltage of the capacitor reaches a predetermined first threshold.

4. The high-voltage generating circuit according to claim 1, wherein the second timing is a timing at which the command from the user is detected.

5. The high-voltage generating circuit according to claim 1, wherein the first timing is a timing at which a cover to open and close an opening of a housing accommodating the laser puncturing unit inside opens.

6. The high-voltage generating circuit according to claim 1, wherein the second timing is a timing at which a cover to open and close an opening of a housing accommodating the laser puncturing unit inside opens.

7. The high-voltage generating circuit according to claim 1, wherein the first timing is a timing at which a presence of skin in a predetermined puncturing position is detected.

8. The high-voltage generating circuit according to claim 1, wherein the second timing is a timing at which a presence of skin in a predetermined puncturing position is detected.

9. The high-voltage generating circuit according to claim 1, further comprising a puncturing timing learner that estimates a time to perform next puncturing based on a time puncturing was previously performed,
    wherein the first timing is a timing estimated by the puncturing timing learner.

10. The high-voltage generating circuit according to claim 1, further comprising a puncturing timing learner that estimates a time to perform next puncturing based on a time puncturing was previously performed,
    wherein the second timing is a timing estimated by the puncturing timing learner.

11. The high-voltage generating circuit according to claim 1, wherein after starting charging the capacitor with the current of the second value, the controller drives the laser puncturing unit at a time the voltage of the capacitor reaches a predetermined second threshold.

12. The high-voltage generating circuit according to claim 1, wherein the controller starts charging the capacitor with the current of the second value and drives the laser puncturing unit based on the command from the user after the voltage of the capacitor reaches a predetermined second threshold.

13. The high-voltage generating circuit according to claim 12, further comprising a buck circuit that regenerates an electric charge charged in the capacitor in a secondary battery based on a control signal output from the controller,
wherein the controller outputs the control signal to the buck circuit when there is no command from the user after a predetermined period of time has passed after the voltage of the capacitor reaches the second threshold.

14. The high-voltage generating circuit according to claim 13, wherein the buck circuit charges the secondary battery with an electric charge in the capacitor until the voltage of the capacitor is equal to or lower than a first threshold.

15. The high-voltage generating circuit according to claim 1 in combination with the laser puncturing unit, the combination comprising a puncturing apparatus.

16. The puncturing apparatus according to claim 15 in combination with a blood sensor that analyzes a blood component exuding from punctured skin, the combination comprising a blood test apparatus.

17. The blood test apparatus according to claim 16, wherein the blood sensor has a film allowing laser light emitted from the laser puncturing unit to pass through.

18. The blood test apparatus according to claim 17, wherein the blood sensor comprises four layers including a substrate, a spacer, a cover and a film.

19. The high-voltage generating circuit according to claim 1, wherein switching from the first stage charging operation to the second stage charging operation occurs only once in a period in which the capacitor is charged from the discharged-state to the amount of charge that is sufficient to drive the laser puncturing unit.

20. A high-voltage generating circuit that drives a laser puncturing unit that oscillates laser light and punctures skin, the high-voltage generating circuit comprising:
a plurality of capacitors that are charged with electric charges and supply power to the laser puncturing unit;
a switch that switches a connection state of the plurality of capacitors between serial connection and parallel connection;
a boost circuit that supplies a current to the plurality of capacitors;
a voltage measuring circuit that measures a voltage of the plurality of capacitors; and
a controller that controls the boost circuit and the switch based on a command from a user or the voltage of the capacitors,
wherein the controller controls the boost circuit to start charging the plurality of capacitors when the plurality of capacitors are connected in parallel by switching the switch at a first timing, and connects the plurality of capacitors in series by switching the switch at a second timing later than the first timing, and
wherein the first timing is a timing at which a cover to open and close an opening of a housing accommodating the laser puncturing unit inside opens.

21. A high-voltage generating circuit that drives a laser puncturing unit that oscillates laser light and punctures skin, the high-voltage generating circuit comprising:
a plurality of capacitors that are charged with electric charges and supply power to the laser puncturing unit;
a switch that switches a connection state of the plurality of capacitors between serial connection and parallel connection;
a boost circuit that supplies a current to the plurality of capacitors;
a voltage measuring circuit that measures a voltage of the plurality of capacitors; and
a controller that controls the boost circuit and the switch based on a command from a user or the voltage of the capacitors,
wherein the controller controls the boost circuit to start charging the plurality of capacitors when the plurality of capacitors are connected in parallel by switching the switch at a first timing, and connects the plurality of capacitors in series by switching the switch at a second timing later than the first timing, and
wherein the first timing is a timing at which a presence of skin in a predetermined puncturing position is detected.

22. A high-voltage generating circuit that drives a laser puncturing unit that oscillates laser light and punctures skin, the high-voltage generating circuit comprising:
a plurality of capacitors that are charged with electric charges and supply power to the laser puncturing unit;
a switch that switches a connection state of the plurality of capacitors between serial connection and parallel connection;
a boost circuit that supplies a current to the plurality of capacitors;
a voltage measuring circuit that measures a voltage of the plurality of capacitors; and
a controller that controls the boost circuit and the switch based on a command from a user or the voltage of the capacitors,
wherein the controller controls the boost circuit to start charging the plurality of capacitors when the plurality of capacitors are connected in parallel by switching the switch at a first timing, and connects the plurality of capacitors in series by switching the switch at a second timing later than the first timing, and
wherein the second timing is a timing at which a presence of skin in a predetermined puncturing position is detected.

23. A high-voltage generating circuit that drives a laser puncturing unit that oscillates laser light and punctures skin, the high-voltage generating circuit comprising:
a plurality of capacitors that are charged with electric charges and supply power to the laser puncturing unit;
a switch that switches a connection state of the plurality of capacitors between serial connection and parallel connection;
a boost circuit that supplies a current to the plurality of capacitors;
a voltage measuring circuit that measures a voltage of the plurality of capacitors;
a controller that controls the boost circuit and the switch based on a command from a user or the voltage of the capacitors; and
a puncturing timing learner that estimates a time to perform a next puncturing based on a time puncturing was previously performed,
wherein the controller controls the boost circuit to start charging the plurality of capacitors when the plurality of capacitors are connected in parallel by switching the switch at a first timing, and connects the plurality of capacitors in series by switching the switch at a second timing later than the first timing, and wherein the first timing is a timing estimated by the puncturing timing leaning learner.

24. A high-voltage generating circuit that drives a laser puncturing unit that oscillates laser light and punctures skin, the high-voltage generating circuit comprising:
- a plurality of capacitors that are charged with electric charges and supply power to the laser puncturing unit;
- a switch that switches a connection state of the plurality of capacitors between serial connection and parallel connection;
- a boost circuit that supplies a current to the plurality of capacitors;
- a voltage measuring circuit that measures a voltage of the plurality of capacitors; and
- a controller that controls the boost circuit and the switch based on a command from a user or the voltage of the capacitors,
- wherein the controller controls the boost circuit to start charging the plurality of capacitors when the plurality of capacitors are connected in parallel by switching the switch at a first timing, and connects the plurality of capacitors in series by switching the switch at a second timing later than the first timing, and
- wherein the controller drives the laser puncturing unit after connecting the plurality of capacitors in series at the second timing.

25. A high-voltage generating circuit that drives a laser puncturing unit that oscillates laser light and punctures skin, the high-voltage generating circuit comprising:
- a plurality of capacitors that are charged with electric charges and supply power to the laser puncturing unit;
- a switch that switches a connection state of the plurality of capacitors between serial connection and parallel connection;
- a boost circuit that supplies a current to the plurality of capacitors;
- a voltage measuring circuit that measures a voltage of the plurality of capacitors; and
- a controller that controls the boost circuit and the switch based on a command from a user or the voltage of the capacitors,
- wherein the controller controls the boost circuit start charging the plurality of capacitors when the plurality of capacitors are connected in parallel by switching the switch at a first timing, and connects the plurality of capacitors in series by switching the switch at a second timing later than the first timing, and
- wherein the controller drives the laser puncturing unit based on the command from the user after connecting the plurality of capacitors in series at the second timing.

26. The high-voltage generating circuit according to claim 25, wherein the controller switches the switch to connect the plurality of capacitors in parallel when there is no command from the user after a predetermined period of time has passed after connecting the plurality of capacitors in series at the second timing.

* * * * *